United States Patent [19]

Loos

[11] Patent Number: 5,782,874
[45] Date of Patent: Jul. 21, 1998

[54] METHOD AND APPARATUS FOR MANIPULATING NERVOUS SYSTEMS

[76] Inventor: Hendricus G. Loos, 3019 Cresta Way, Laguna Beach, Calif. 92651

[21] Appl. No.: 788,582

[22] Filed: Jan. 24, 1997

Related U.S. Application Data

[63] Continuation-in-part of Ser. No. 447,394, May 23, 1995, abandoned, which is a continuation of Ser. No. 68,748, May 28, 1993, abandoned.

[51] Int. Cl.$^6$ .................................................. A61N 1/40
[52] U.S. Cl. ........................................................ 607/2
[58] Field of Search ............................ 607/1, 2, 39, 45, 607/46, 62, 75, 115, 152; 600/26; 602/2; 128/897, 908

[56] References Cited

U.S. PATENT DOCUMENTS 1,973,911   9/1934   Ruben .......................... 607/152

*Primary Examiner*—William E. Kamm

[57] ABSTRACT

Apparatus and method for manipulating the nervous system of a subject through afferent nerves, modulated by externally applied weak fluctuating electric fields, tuned to certain frequencies such as to excite a resonance in certain neural circuits. Depending on the frequency chosen, excitation of such resonances causes relaxation, sleepiness, sexual excitement, or the slowing of certain cortical processes. The weak electric field for causing the excitation is applied to skin areas away from the head of the subject, such as to avoid substantial polarization current densities in the brain. By exploiting the resonance phenomenon, these physiological effects can be brought about by very weak electric fields produced by compact battery-operated devices with very low current assumption. The fringe field of doublet electrodes that form a parallel-plate condenser can serve as the required external electric field to be administered to the subject's skin. Several such doublets can be combined such as to induce an electric field with short range, suitable for localized field administration. A passive doublet placed such as to face the doublet on either side causes a boost of the distant induced electric field, and allows the design of very compact devices. The method and apparatus can be used by the general public as an aid to relaxation, sleep, or arousal, and clinically for the control and perhaps the treatment of tremors and seizures, and disorders of the autonomic nervous system, such as panic attacks.

9 Claims, 5 Drawing Sheets

$$E = F \frac{AV}{4\pi s^3}$$

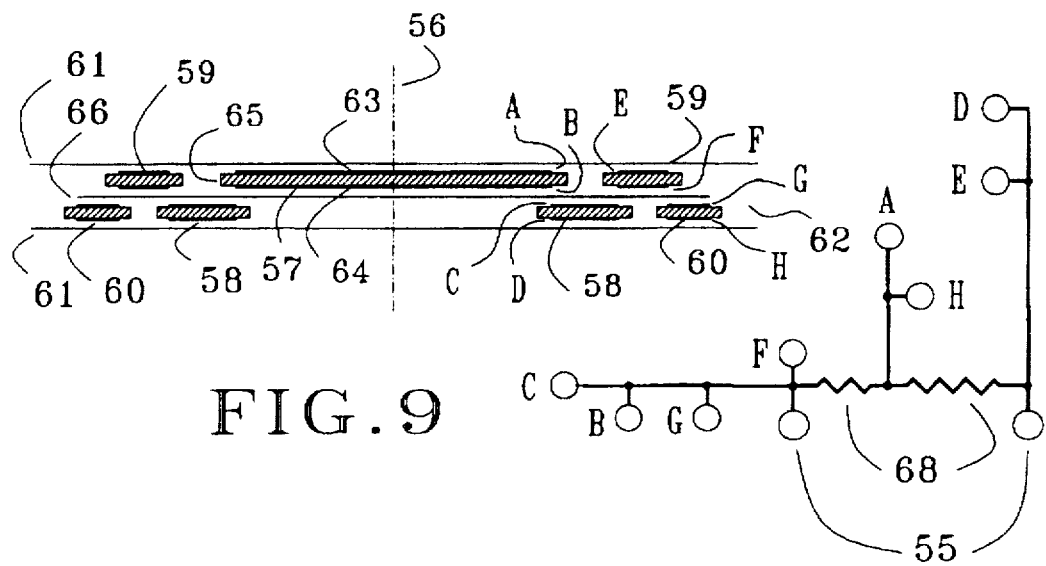
FIG.9
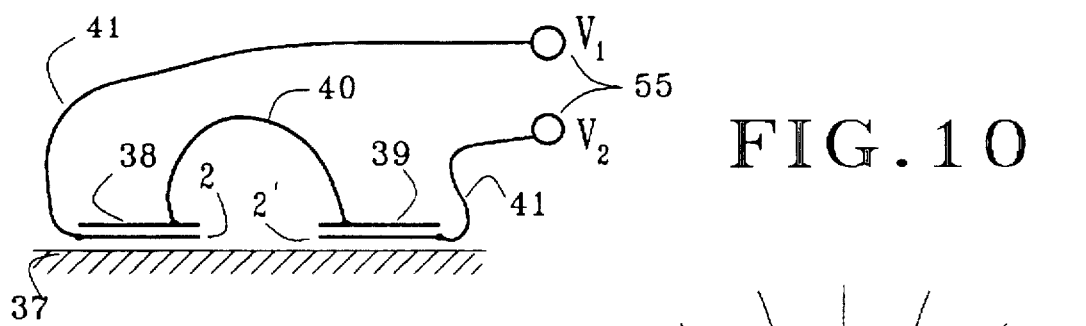
FIG.10
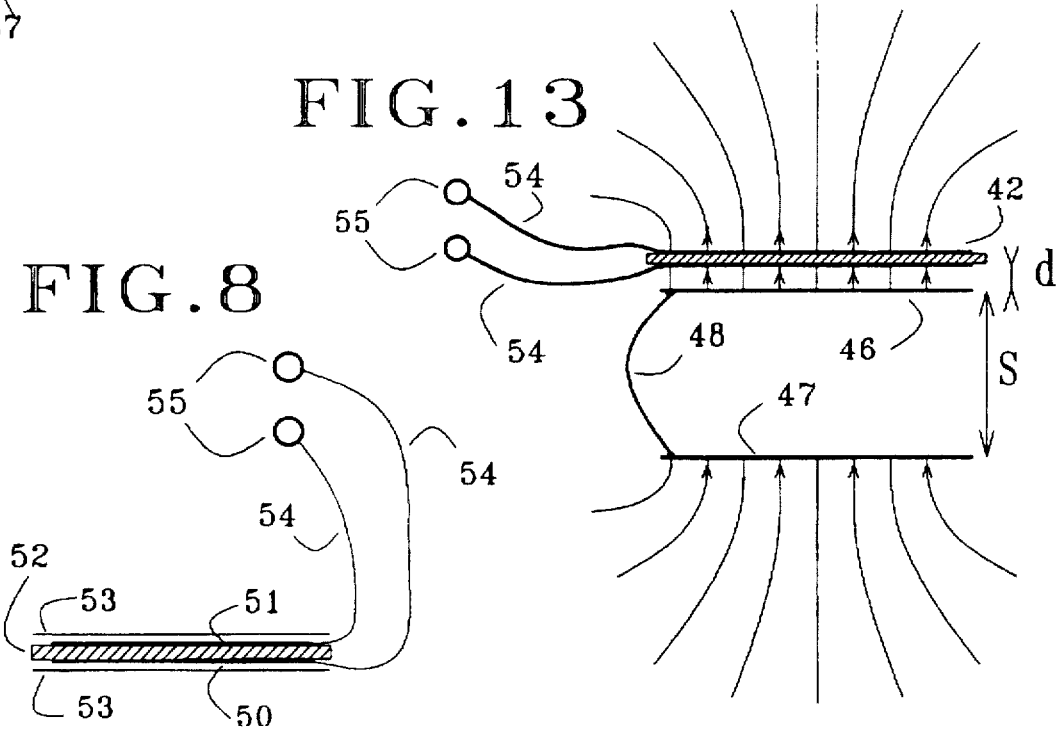
FIG.13
FIG.8

METHOD AND APPARATUS FOR MANIPULATING NERVOUS SYSTEMS

This application is a Continuation-in-part of Ser. No. 08/447,394, May 23, 1995, abandoned which is a continuation of Ser. No. 08/068,748, May 28, 1993, abandoned.

BACKGROUND OF THE INVENTION

The invention relates to electrical neurostimulation, wherein electric currents are passed to the brain, the spinal cord, an organ, or peripheral nerves [1–3]. Such stimulation has been used with various degrees of success for anesthesia, induction of relaxation and sleep, as well as for the treatment of pain, intractable epilepsy, behavioral disorders, movement disorders, and cardiac arrhythmia. The electric current is usually delivered by contact electrodes i.e., electrodes that are in Ohmic contact with the biological tissue. An exception is the capacitor electrode of Guyton and Hambrecht [4], which consists of an implanted porous tantalum disc with a thin insulating coating of tantalum pentoxide. After implantation, the pores fill with extracellular fluid and thus present a large capacitive interface to the fluid. The electrode is capable of delivering sizable currents to tissue without causing accumulation of electrochemical byproducts. Mauro [5] has proposed another capacitor electrode in which one of the "plates" of a large capacitor is formed by an electrolyte that is in Ohmic contact with the tissue, via a thin tube. In both these cases the capacitance employed is large, such as to pass currents of a magnitude and duration large enough to cause firing of the nerves, as expressed by the strength-duration curve with typical times of 0.1 ms and currents of the order of 1 mA [6,7]. The nerves fire as a result of substantial depolarization of the nerve membrane by the applied electric current, a process here called classical nerve stimulation.

An area of neurostimulation that has attracted much attention is the induction of relaxation and sleep. One method, called Cranial Electric Stimulation (CES) involves passing an alternating current through the brain via contact electrodes attached to the head or held in the mouth. With properly chosen strength and frequency, these currents may excite or support brain waves that accompany deep sleep. The method has been explored extensively in the Former Soviet Union, under the name "Electrosleep".

A commercially available device is the Japanese "Sleepy" [8], which generates for one hour square pulses of 4 V and 0.2 ms duration, with a frequency that sweeps from 14 to 0 Hz, every 3 minutes. The device requires contact electrodes placed on the head. Other commercial CES devices [9] are Alpha Stim, Mindman, and Endo Stim, which all require contact electrodes attached to the head.

Electric currents in biological tissue may also be induced by an electric field that is generated in the space outside the subject. The external electric field is set up by applying an electric potential between field electrodes that do not have Ohmic contact with the tissue. Of course the arrangement may be seen as a form of capacitive coupling, but with capacitances very much smaller than in Mauro [5] or Guyton and Hambrecht [4]. There is also an important practical difference, in that no bodily contact with any part of the apparatus is required for the electric field application by field electrodes.

A neurological effect of external electric fields has been mentioned by Norbert Wiener [10], in discussing the bunching of brain waves through nonlinear interactions. The electric field was arranged to provide "a direct electrical driving of the brain" [10]. Wiener describes the field as set up by a 10 Hz alternating voltage of 400 V applied in a room between ceiling and ground.

Brennan [11] describes an apparatus for alleviating disruptions in the circadian rythms of a mammal, in which an external alternating electric field is applied across the head of the subject. The voltage applied to the electrodes is specified as at least 100 V, and the peak to peak value of the electric field as at least 590 V/m in free air before deploying the electrodes across the head of the subject. The frequency of the alternating electric field is in the range from 5 Hz to 40 Hz. Brennan states that the method is aimed at subjecting at least part of the subject's brain to an alternating electric field, in the belief that this would stimulate an influx of $Ca^{2+}$ ions into nerve endings, which in turn would "regulate and facilitate the release of neurotransmitters". Embodiments mentioned include electrodes arranged in a head cap, in a bed, or mounted on the walls of a room. It should be noted that electric polarization of the head causes the field strength in the narrow space between electrode and skin to be about a factor h/2d larger than the free-air field strength, h being the distance between the electrodes and d the spacing between electrode and skin. For h=17 cm and d=5 mm the factor comes to 17, so that with the specified free-air field of at least 590 V/m, the field in the gap between electrode and skin is at least 10 KV/m peak to peak.

A device that involves a field electrode as well as a contact electrode is the "Graham Potentializer" mentioned in Ref. [9]. This relaxation device uses motion, light, and sound as well as an external alternating electric field, applied predominantly to the head. The contact electrode is a metal bar in Ohmic contact with the bare feet of the subject; the field electrode has the form of a hemispherical metal headpiece placed several inches from the subject's head. According to the brief description in [9], a signal of less than 2 Volts at a frequency of 125 Hz is applied between the field electrode and the contact electrode. In this configuration, the contact electrode supplies to the body the current for charging the capacitor formed by the head-piece field electrode and the apposing skin area. The resulting electric field stands predominantly in the space between the head piece and the scalp.

In the three external field methods mentioned, viz., Wiener [10], Brennan [11], and Graham [9], the electric field is applied to the head, thereby subjecting the brain to polarization currents. These currents run through the brain in a broad swath, with a distribution determined by nonuniformities of conductivity and permittivity. The scale of the current density can be conveniently expressed by the maximum value, over the skin of the head, of its component perpendicular to the local skin. This scale is easily for sinusoidal fields as the product of radian frequency, permittivity, and maximum amplitude of the external field on the head. Using Brennan's [11] lowest frequency of 5 Hz, his minimum required free-air field strength of 590 V/m, and the factor 17 as estimated above to account for polarization of the head by the applied field, the scale of the polarization current density in the brain comes to about 280 $pA/cm^2$. In the absence of an understanding of the neurological effects involved, it is prudent to avoid exposing the brain to current densities of such scale, and impose as a limit 1/4000 times the scale calculated for Brennan's patent. Polarization current densities in the brain with a scale in excess of 70 $fA/cm^2$ are henceforth considered substantial. It is the object of the present invention to obtain a method and apparatus for manipulating the nervous system by external electric fields without causing substantial polarization current densities in the brain.

3

The use of electric fields raises concerns about possible health effects. Such concerns have been widely discussed in the media in regard to electric power lines and electric apparatus [12]. Answering the pertinent questions by objective research will take time, but meanwhile governments have been setting guidelines for safe limits on field strengths. At present, the strictest conditions of this sort are the Swedish MPRII guidelines. Magnetic fields are of no concern here, because the currents involved are so small. However, the electric field strength must be considered, since even at low voltages strong electric fields can result from field electrodes placed close to the skin. With respect to extremely low frequency electric fields, the MPRII guidelines limit the field strength to 25 V/m in the frequency range from 5 Hz to 2 Khz. In the Brennan patent [11] the minimum field strength of 590 V/m violates the guidelines by a factor 23; when polarization effects are accounted for, the factor is about 400.

It is a further object of the present invention to manipulate the nervous system by external electric fields that are in compliance within the MPRII guidelines.

Brennan [11] stipulates voltages of at least 100 V, and as high as 600 V for the preferred embodiment. Generation of such voltages requires a voltage multiplier stage, if practical battery operation is desired. This increases the current drain and the size of the generator. The large voltages also raise safety concerns. It is yet a further object of the present invention to manipulate the nervous system by external electric fields, using low voltages that are generated by a small and safe battery-operated device with low current consumption.

SUMMARY

Experiments have shown that weak electric fields of frequency near ½ Hz applied externally to the skin of a subject can cause relaxation, doziness, ptosis of the eyelids, or sexual excitement, depending on the precise frequency used. In these experiments the electric field was applied predominantly to skin areas away from the head, thereby avoiding substantial polarization current densities in the brain. Apparently, the external electric field somehow influences somatosensory or visceral afferent nerves, which report the effect to the brain. Although the mechanism whereby the field acts on the afferents is unknown, the effect must take the form of a slight modulation of the firing patterns of the nerves, because the polarization current densities induced by the field are much to small to cause firing of the nerve. If the applied external field is periodic, so will be the modulation of the firing patterns of affected afferent fibers, and the brain is then exposed to an evoked periodic signal input. Apparently, this signal input influences certain resonant neural circuits, the state of which has observable consequences. Since the resonances are excited through somatosensory or visceral afferents, they are called "sensory resonances".

Besides the resonance near ½ Hz that affects the autonomic nervous system, we have also found a resonance near 2.4 Hz which slows certain cortical processes. For both resonances the electric field strength on the skin must lie in a certain range of values for the physiological effects to occur. This "effective intensity window" can be determined accurately for the 2.4 Hz resonance, by measuring the time needed to count silently backward from 100 to 70.

The effective intensity window depends on the number of afferents modulated by the field. This "bulk effect" is important for the proper use of the invention, and has therefore

4 been explored in preliminary experiments. At the lower boundary of the windows the external field strengths are very small, down to 10 mV/m when a large skin area is exposed to the field. The fact that very small external field strengths suffice for excitation of sensory resonances through modulation of afferents allows the use of small battery-powered electric field generators that can be used conveniently by the general public as an aid to relaxation, sleep, or sexual excitement, and clinically for the control and perhaps the treatment of tremors and seizures, and disorders of the autonomic nervous system such as panic attacks.

Compliance of the devices with the MPRII guidelines on field limits in the ELF and VLF frequency bands is easily achieved.

The field generators shown involve simple low-voltage generators based on 555-type timer chips, and field electrodes that are small enough to fit together with the generator in a single small casing, such as a powder box. A particularly compact field electrode configuration is the doublet, which has the structure of a parallel-plate condensor; the fringe field of the doublet is used for the ecitation of sensory resonances in the subject.

To be effective, the fluctuating electric field need not be sinusoidal or even periodic. The field may have a complicated spectral power density, as long as the dominant frequency is close to the resonant frequency of the sensory resonance of interest. A simple chaotic voltage generator based on two timer chips is shown. Field electrode configurations of practical interest include a shielded pair for producing a sharply localized electric field on two selected skin areas, and a multipole field electrode which has a very short range. Although the mechanism of electric field modulation is unknown, candidates for cutaneous receptors that may be susceptible to this modulation are indicated.

DESCRIPTION OF THE DRAWINGS

FIG. 8 shows a doublet field electrode.

FIG. 9 depicts a multipole field electrode for producing a short-range electric field.

FIG. 10 shows schematically a shielded pair of electrodes.

5

FIG. 13 shows a doublet with distant field enhancer.

Figure 14:
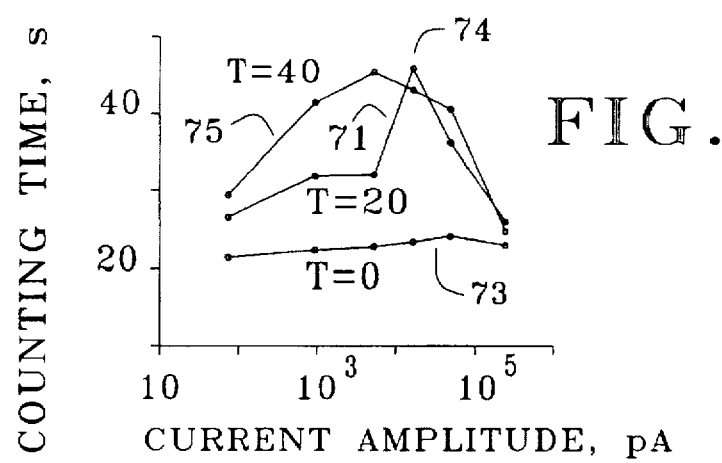

FIG. 14 shows the effective intensity window for currents passed by contact electrodes to the skin overlaying the vagus nerve.

Figure 15:
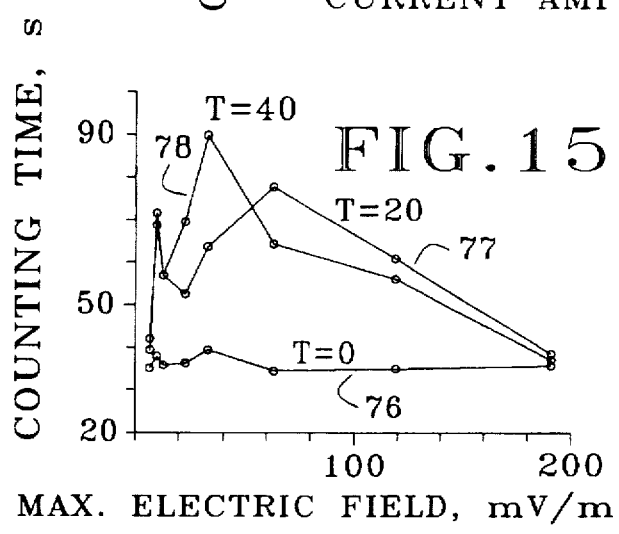

FIG. 15 shows the effective intensity window for large skin area exposure to the field from a doublet placed some distance from the subject.

Figure 16:
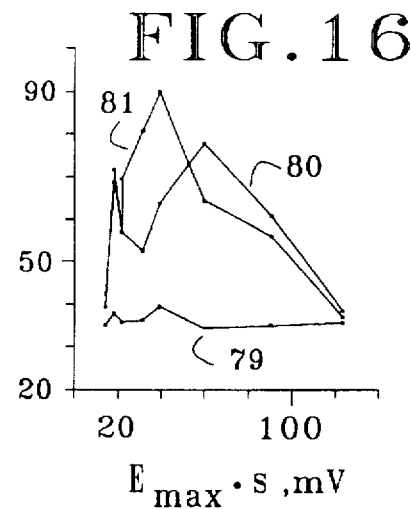
Figure 17:
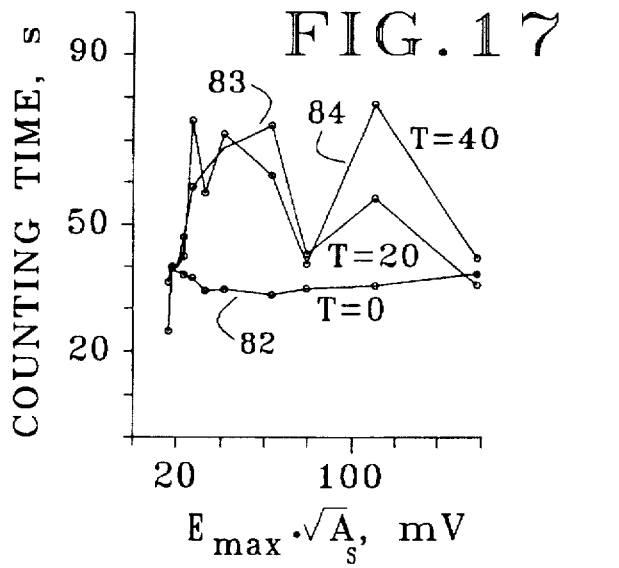
Figure 18:
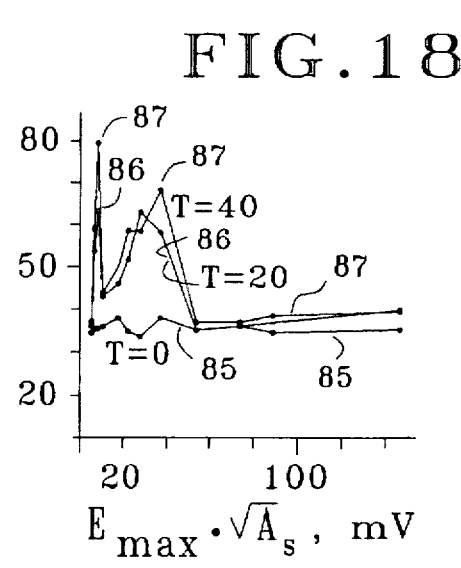

FIG. 16 is a replot of the data of FIG. 15, to serve in a comparison with the data of FIGS. 17 and 18.

FIG. 17 shows the effective intensity window for an experiment using a shielded electrode pair placed on the thighs.

FIG. 18 shows the effective intensity window for an experiment using a shielded electrode pair placed on the finger tips.

DETAILED DESCRIPTION

The invention is based on the discovery, made in our laboratory, that neurological effects can be induced by weak external electric fields of a precisely tuned frequency near ½ Hz, when applied to skin areas away from the head. The observed effects include ptosis of the eyelids, relaxation, drowziness, the feeling of pressure at a centered spot on the lower edge of the brow, seeing moving patterns of dark purple and greenish yellow with the eyes closed, a tonic smile, a tense feeling in the stomach, and sexual excitement, depending on the precise frequency used. These effects were observed initially for external field strengths in the range from 1 to 25 V/m, but recent experiments have shown effects with much weaker and stronger fields.

In these experiments the polarization current densities produced in biological tissue by the applied external electric field are much too small to cause classical nerve stimulation, yet a central nervous system response is evoked. Experiments have shown that signal pathways other than afferent nerves are not involved. It follows that weak external electric fields can evoke some sort of signal that is carried by afferent nerves. Since classical nerve stimulation cannot occur, these signals must have the form of a modulation of spontaneous firing patterns. The simplest such modulation is frequency modulation (fm), but more subtle modulation modes [26] may be involved. For simplicity of description however, we will refer to the modulation as fm. In our experiments the modulation depth is very small, but for field frequencies that are close to a resonant frequency of receptive neural circuits the weak incoming fm signal can evidently cause excitation of the resonance with observable consequences. Since the applied fields are much too weak to cause nerves to fire, the sensory and visceral receptors and afferents susceptable to modulation must exhibit spontaneous firing.

Since the resonances are excited through somatosensory or visceral afferent nerves, they are here called sensory resonances. The sensory resonance near ½ Hz involves the autonomic nervous system and is therefore called the ½ Hz autonomic resonance.

Exploitation of sensory resonances and reliance on modulation of spontaneous firing patterns rather than classical nerve stimulation makes it possible to manipulate the nervous system with very small electric fields, induced by low voltages. Moreover, employing the natural pathways of afferent nerves into the brain allows application of the field to skin areas away from the head. The invention thereby meets the stated objects of providing manipulation of the nervous system without causing substantial polarization

6 current densities in the brain, compliance with MPRII field limits, and use of a low-voltage battery-operated generator with low current consumption.

The invention provides a method and apparatus for manipulating the nervous system of human subjects. Such manipulation comprises relaxation and the induction of sleep or arousal, as well as the control and perhaps the treatment of tremors, seizures, and disorders resulting from malfunctions of the autonomic nervous system, such as panic attacks.

In the early experiments the excitation of the sensory resonance occurred through modulation of cutaneous nerves by the applied external electric field. In later experiments with larger field strengths, similar physiological effects have been obtained by applying the field to the skin overlaying the vagus nerve or the sciatic nerve. It appears that excitation of sensory resonances can be achieved through any afferent pathway, provided that it is broad.

A new sensory resonance has been found at 2.4 Hz, characterized by a pronounced increase in the time needed for counting silently backward from 100 to 70. Prolonged exposure to the 2.4 Hz excitation is found to have a sleep-inducing and dizzying effect. Recent experimental results will be discussed towards the end of the specification.

The equipment suitable for the generation of the weak electric fields used for the modulation of afferent nerves consists of field electrodes and a voltage generator. The field electrodes can simply be conductive foils, wires, or meshes that may optionally be covered on one or both sides with an insulating layer. The field electrodes are to be electrically connected to the generator, but insulated from the subject. The voltage generator is to produce a low fluctuating voltage. The time dependence of the fluctuating voltage need not be sinusoidal or even periodic, but may have a complicated spectrum, as long as the dominant frequency of the voltage is at or near the resonance frequency for the sensory resonance of interest, or can be tuned to this effect; a tuning range from 0.1 to 3 Hz was used for the early experiments in which the ½ Hz resonance was found. The dominant frequency is here defined as the frequency at the global maximum of the spectral power density. In the rare case that there is more than one such maximum, the dominant frequency is formally taken as the least of the frequencies for the global maxima. The dominant frequency of the output of a generator can be easily measured, and those skilled in the art can readily design a generator with a specified or tunable dominant frequency and desired spectral properties. Harmonic content needs to be considered for compliance with the MPRII guidelines, if the amplitude of the field applied to the skin is large. An automatic shutoff can be provided, such as to limit the duration of field application.

It has been found that a single ½ hour application of the field is usually sufficient to induce sleep, if the frequency of the wave is tuned correctly for the individual to a frequency near ½ Hz. Shorter application times are typically sufficient for inducing relaxation. The effects of the applied electric field are usually noticeable after half a minute or so.

Figure 1:
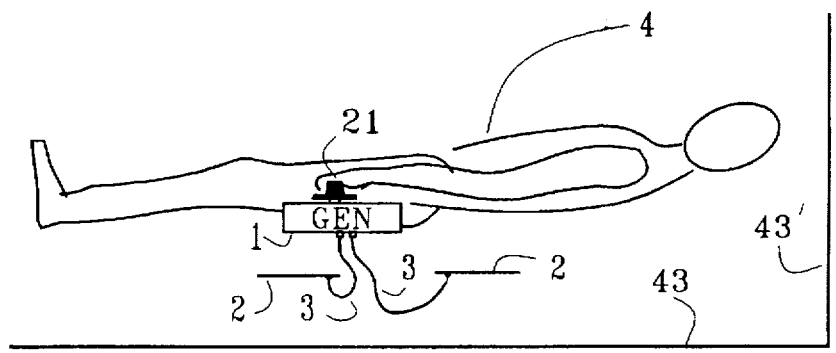
FIG. 1 depicts a preferred embodiment, and shows the deployment of field electrodes external to the body of the subject.
Figure 2:
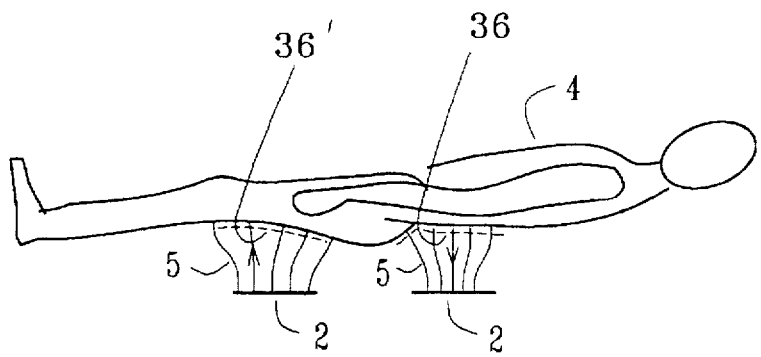
FIG. 2 illustrates the electric field generated between the field electrodes and the subject's body.

A preferred embodiment of the invention is shown in FIG. 1, where the voltage generator 1, labeled as GEN, is connected to the field electrodes 2 by wires 3; the field electrodes 2 are positioned away from the subject 4. The voltage generator may be tuned manually with the tuning control 21. As an option, sheet conductors 43 and 43' such as aluminum foils may be placed near the subject in order to diminish interference from a 60 Hz or 50 Hz house field, to be discussed. Referring to FIG. 2, application of a voltage between the field electrodes 2 produces an electric field 5 between field electrodes 2 and the subject 4, for the case that the sheet conductors 43 and 43' of FIG. 1 are absent. The field is applied predominantly to skin areas away from the head of the subject; in the setup of FIG. 1 these areas comprise skin area 36 on the hips, buttocks, and lower back, and skin area 36' on the back side of the thighs and knees.

Figure 3:
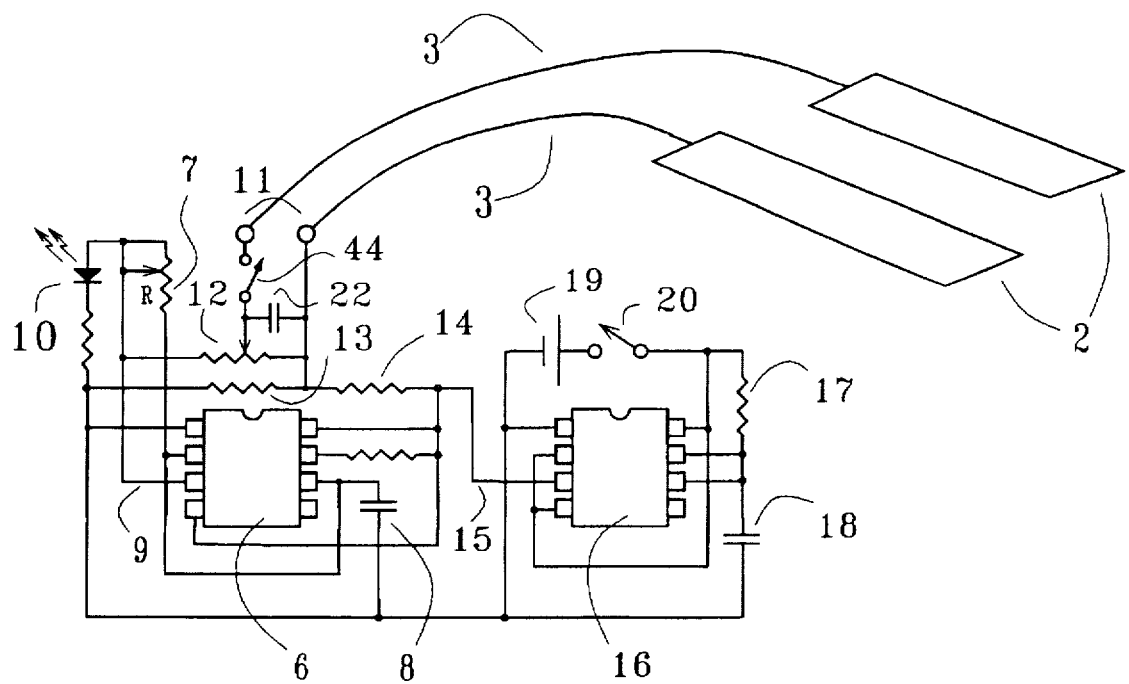
FIG. 3 shows an embodiment which generates an electric field that fluctuates as a rounded square wave, and includes an automatic shutoff.

A suitable voltage generator, built around two RC timers, is shown in FIG. 3. Timer 6 (Intersil ICM7555) is hooked up for astable operation; it produces a square wave voltage with a frequency determined by resistor 7 and capacitor 8. The square wave voltage at the output 9 drives the LED 10, and appears at one of the output terminals 11, after voltage division by potentiometer 12. The other output terminal is connected to an intermediate voltage produced by the resistors 13 and 14. As a result, the voltage between the output terminals 11 alternates between positive and negative values. Automatic shutoff of the voltage that powers the timer, at point 15, is provided by a second timer 16 (Intersil ICM7555), hooked up for monostable operation. The shutoff occurs after a time interval determined by resistor 17 and capacitor 18. Timer 16 is powered by a 3 V battery 19, controlled by the switch 20. The output terminals 11 are connected to the field electrodes 2 by conductors 3. The resistors 13 and 14 not only serve as a voltage divider that gives the intermediate voltage needed to produce an alternating square wave, but these resistors also provide current limitation. A further decrease of the currents induced in the subject is caused by the output capacitor 22, in a manner to be discussed. There is the option of including a switch 44 in the output circuit, in order to prevent polarization of the electrode assembly by a 60 Hz or 50 Hz house field when the device is inactive, to be discussed.

Figure 4:
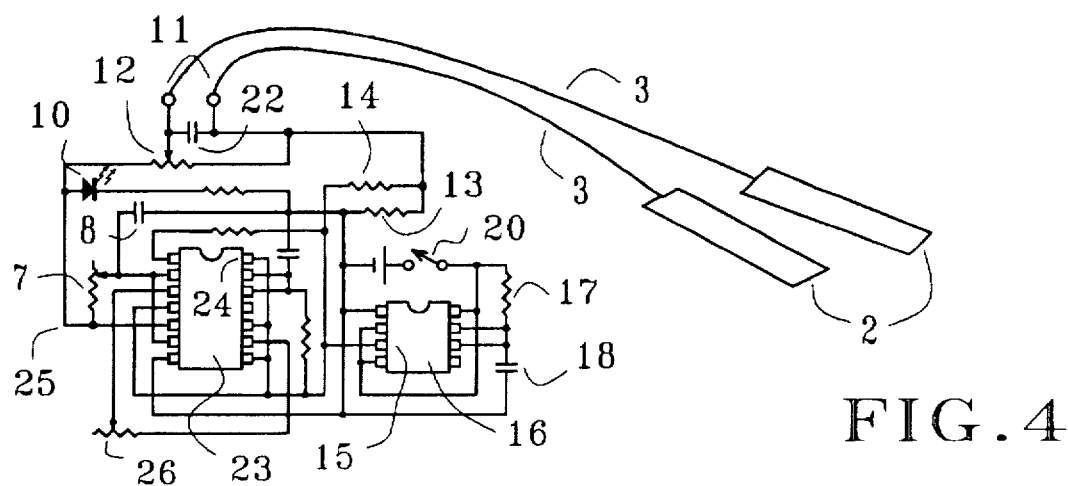
FIG. 4 shows an embodiment which generates an electric field that fluctuates as a rounded square wave, and which includes an automatic frequency shift and automatic shutoff.

A time variation of frequency may be accomplished by manipulating the control voltage of one section of a dual timer with the output of the other section. An embodiment for this type of operation is shown in FIG. 4. The dual timer 23 (Intersil ICM7556) is powered at point 24 by voltage from the output 15 of timer 16 (Intersil ICM7555), which serves as an automatic shutoff after a time interval determined by resistor 17 and capacitor 18. The timer operation is started by closing switch 20. The voltage at output 25 of the dual timer 23 drives the LED 10, and is applied, via the variable resistor 12, to one of the outputs 11 of the voltage generator. Resistors 14 and 13 serve to provide an intermediate voltage at the other output terminal 11, such as to result in a potential difference between the output terminals that alternates between positive and negative values of substantially equal magnitudes. The frequency of the square wave voltage at point 25 depends on resistor 7 and capacitor 8. The frequency is also influenced by the control voltage applied to the timer. A frequency upshift can be obtained by applying the output of the second section of the dual timer 23 to the control voltage pin of the first timer section, via resistor 26. This second timer section is hooked up for monostable operation. The output terminals 11 are connected by conductors 3 to the field electrodes 2, which are pieces of aluminum foil, covered by insulating tape on both sides.

The automatic shutoff and time variation of the frequency are examples of automatic control of the fluctuating voltage generated by the generator.

Low frequencies can be monitored with an LED 10 of FIG. 3. The LED blinks on an off with the square wave, and doubles as a power indicator. The frequency can be determined by reading a clock and counting LED light pulses. For higher frequencies a monitoring LED can still be used, if it is driven by a wave obtained by frequency division of the generator output wave.

The voltage generators discussed above have oscillators of the RC type, but other types of low-voltage oscillators can be used as well. For instance, the voltage generator can be built as a digital device, in which a square wave output is derived from a clock signal by means of frequency division. Chaotic signals, time variation of frequency, programmed frequency sequences, automatic turn on and shutdown, frequency adjustment, and frequency monitoring may also be accomplished digitally. A computer that runs a simple timing program can be used for the generation of all sorts of square waves that can be made available at a computer port. An economic and compact version of such arrangement is provided by the Basic Stamp [30], which has an onboard EEPROM that can be programmed for the automatic control of the fluctuating voltage generated, such as to provide desired on/off times, frequency schedules, or chaotic waves. In the interest of controlling polarization current peaks or complying with MPRII guidelines, the square waves can be rounded by RC circuits, and further smoothed by integration and filtering. In this manner, near-sinusoidal output can be achieved. Such output can also be obtained with a digital sine-wave generator based on a walking-ring counter [31], or with a waveform generator chip such as the Intersil ICL8038. Analog circuits for tunable sine wave generators based on LC oscillators with passive inductance and capacitance are not practical because of the very large component parameter values required at the low frequencies involved. Large inductances can be produced by a compact active stage, or one can use two separate RC phase shift circuits connected in a loop with an amplitude limiter [32]. Tuning may be done with a single potentiometer.

Applications are envisioned in which the field electrodes are driven with a fluctuating voltage that is chaotic. Such a voltage is here defined as a signal for which the times of zero crossings or peaks, or both, form a pseudo-random sequence. A simple example is provided by a square wave for which the transition time intervals form a pseudo-random sequence, within upper and lower limits. The brain is adaptive, but the chaotic transitions are difficult to learn and anticipate, and therefore a field with a slightly chaotic square wave can thwart habituation. A sensory resonance can still be excited by such a wave, if the dominant frequency of the wave is close to the resonant frequency. The chaotic wave can also be used to upset pathological oscillatory modes in neural circuitry, such as to control tremors in Parkinson patients.

Figure 5:
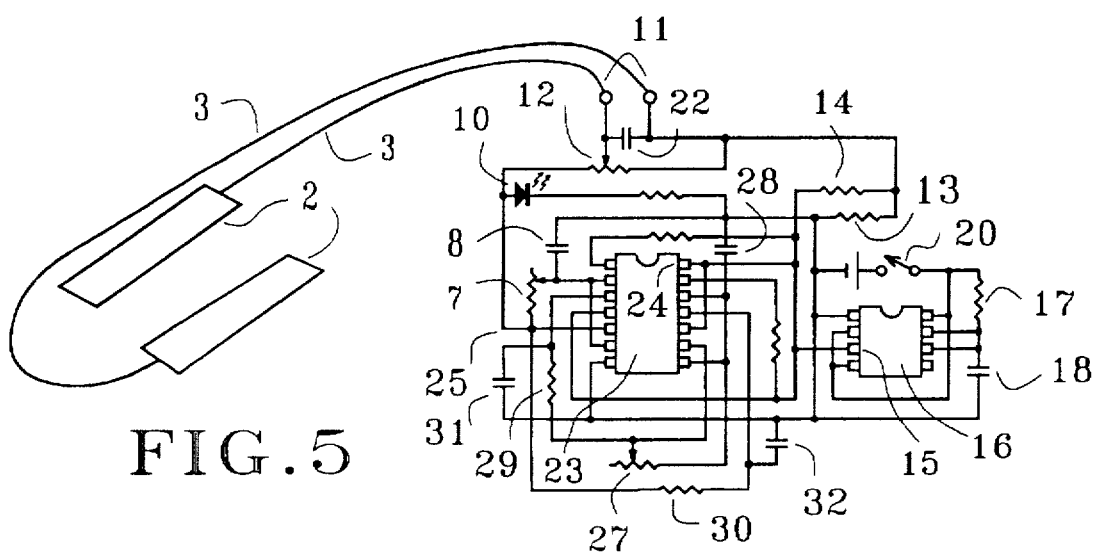
FIG. 5 shows an embodiment which generates an electric field that fluctuates as a rounded square wave with a chaotic time dependence, and which includes an automatic shutoff.

An embodiment which involves a chaotic square wave electric field is shown in FIG. 5. The dual timer 23 (Intersil ICM7556) is powered, at point 24, by the output 15 of timer 16 (Intersil ICM7555), hooked up for monostable operation, such as to provide automatic shutoff after a time determined by resistor 17 and capacitor 18. Operation of timer 16 is started by closing switch 20. Both sections of the dual timer 23 are hooked up for bistable operation, with slightly different RC times. The voltage at output 25 of the first timer section is used to drive the LED 10; after voltage division by the variable resistor 12, the voltage is applied to one of the outputs 11. The other output 11 is an intermediate voltage from the voltage divider formed by resistors 14 and 13. The outputs 11 are connected to the field electrodes 2 through conductors 3. The RC time of the first timer section is determined by resistor 7 and capacitor 8. The RC time of the second timer section is determined by resistor 27 and capacitor 28. The two timer sections are coupled by connecting their outputs crosswise to the control voltage pins, via resistors 29 and 30, with capacitors 31 and 32 to ground. For a proper range of component values, easily found by trial and error, the square wave output of each of the timer sections is chaotic.

Figure 6:
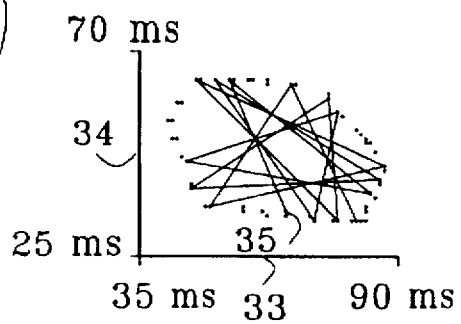
FIG. 6 shows the map of time intervals between consecutive transitions of the chaotic square wave generated by the circuit of FIG. 5.

An example for chaotic output is shown in FIG. 6, where the points plotted correspond to transitions (edges) of the square wave. Abscissa 33 and ordinates 34 of a plotted point are time durations between consecutive transitions of the square wave output; for any transition, the abscissa is the time to the preceding transition, and the ordinate is the time to the next transition. Starting with transition 35, consecutive transitions are found by following the straight lines shown. The transition times follow a pseudo random sequence, with some order provided by the oval attractor. The results shown in FIG. 6 were measured for the device of FIG. 5, with the following component values: $R_7=1.22$ $M\Omega$, $R_{27}=1.10$ $M\Omega$, $R_{29}=440$ $K\Omega$, $R_{30}=700$ $K\Omega$, $C_8=0.68$ $\mu f$, $C_{28}=1.0$ $\mu f$, $C_{31}=4.7$ $\mu\mu f$, and $C_{32}=4.7$ $\mu f$. In the above list, $R_i$ is the resistance of component i in FIG. 5, and $C_j$ is the capacitance of component j.

Tests with a subject who is not a Parkinson patient, but who has a hand tremor of another origin, have shown good control of the tremor by a square wave electric field with the chaotic time dependence shown in FIG. 6. The device of FIG. 5 was used in these tests, with electrodes placed vertically on two opposite vertical sides of the seat cushion of an easy chair.

In the present invention, the external field is applied predominantly to certain selected areas of the skin of the subject, such as the areas as 36 and 36' in FIG. 2. Areas of predominant field application are here defined to consist of all points of the skin at which the absolute value of the resultant field strength is at least twice the average over the skin. The resultant field includes the field produced by polarization charges on the skin of the subject. The resultant field is perpendicular to the skin when the polarization keeps up with changes in the applied field, as is the case for the low frequencies involved, if sharp transitions are avoided.

Figure 7:
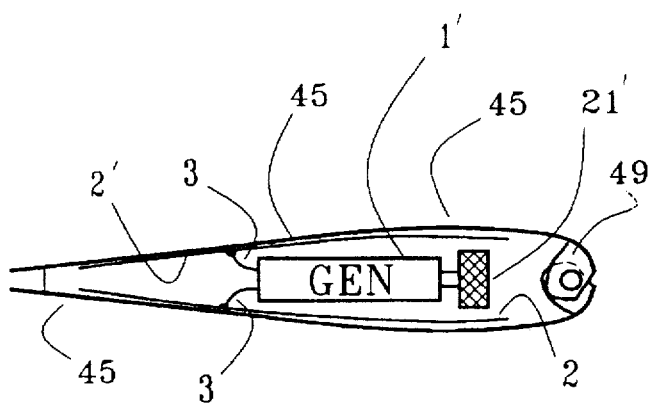
FIG. 7 shows an embodiment with the field electrodes and generator contained in a powder box.

Of convenience in social settings is an embodiment in which the two field electrodes and the signal generator are contained in a single casing such as a small box, purse, powder box, or wallet. An embodiment is shown in FIG. 7, where the generator 1' with tuning control 21' is placed inside a powder box casing 45 with hinge 49. The field electrodes 2 and 2' are contained in the casing 45. The field electrodes 2 are connected to the generator 1' by conductors 3. For brevity, field electrodes mounted on the outside surface of a casing are considered as contained in the casing.

The peak-to-peak variation of the output voltage of the voltage generators discussed above cannot exceed 16 V, because of supply voltage limitations for the CMOS timer chip. However, much lower output voltages suffice for most applications. An output voltage of 2.4 V peak to peak is adequate for the setup of FIG. 1. Such an output voltage is provided by the signal generators of FIGS. 3 and 4, when powered by a 3 V battery. Such small voltages suffice even for embodiments in which the generator and field electrodes are mounted in a single small casing, in spite of the small area available for the electrodes.

An electric field outside the body of the subject is called an external electric field.

In applications of modulation of cutaneous nerves by an external electric field there is usually also present a 60 Hz or 50 Hz house field, an electric field emanating from house wiring, electric apparatus and electric power lines. House fields can have considerable strength; Becker and Marino [15, table 10.4] list the electric field, at 1 ft distance from an electric blanket, broiler, refrigerator, food mixer, hairdryer, and color TV, respectively as 250, 130, 60, 50, 40, and 30 V/m. The electric field 1 ft away from a light bulb is listed as 2 V/m. The house field may cause inadvertent modulation of cutaneous nerves. In distinction with this inadvertent modulation, there is the purposeful modulation which is the subject of the present invention. The house field intensities mentioned above suggest that the house field may interfere with the purposeful modulation. The interference can be diminished by reducing the strength of the house field incident on the subject. This may be done by placing near the subject a sheet conductor oriented roughly parallel with the local house field. An example is shown in FIG. 1, where a sheet conductor in the form of aluminum foils 43 is placed against the underside of the bed, and a continuation 43' of the aluminum foil covers the back of the headboard. The house-field-diminishing effect of a properly placed and oriented sheet conductor can be readily understood as due to electric polarization of the sheet conductor by the house field.

There further is concern about the effect of house field induced electric polarization of the electrode assembly, that may occur at times when no external electric field is being generated by the apparatus, although the field electrodes are electrically connected through the device. This state occurs during most of the night, if the apparatus of FIGS. 3 or 4 is used as a sleeping aid with permanently placed field electrodes, after the automatic shutoff has cut the power to the oscillator. Of concern is the circuit comprised of the two field electrodes, their connections to the signal generator, and pertinent output circuitry in the signal generator. Referring to FIG. 3, it is seen that this circuit includes the capacitor 22 and part of the potentiometer 12. The house field generally induces polarization currents in this circuit. The resulting polarization charges on the field electrodes induce an electric field with a nonuniformity scale comparable to the electrode spacing. This 60 Hz field may cause modulation of the same afferent nerves as those involved in the purposeful modulation by the apparatus field. The inadvertent modulation may cause weak fm signals of 60 Hz frequency in receptive neural circuitry, and the signals may be so weak as to sneak by nuisance-guarding circuitry. The unwanted signals may be diminished by using the house-field-diminishing sheet conductor described above. Alternatively, or in addition, polarization of the electrode assembly by the house field may be prevented by breaking the electric connection between the field electrodes by means of a switch (44 in FIG. 3) in one of the output leads of the signal generator. This switch may be ganged with the power switch.

The external electric field must be predominantly applied to skin regions away (at least 10 cm) from the head of the subject. Furthermore, substantial polarization current densities in the subject's brain must be avoided. The scale of these current densities is expressed here for sinusoidal fields as the product of permittivity, radian frequency of the field, and maximum external electric field amplitude on the head; this product should not exceed 70 fA/cm$^2$. Satisfying this condition and that of predominant field application to skin areas away from the head requires calculation of external field strengths on the subject's skin, for the field electrode configuration and deployment considered. This can be done along the following lines.

First, the electric field produced by a field electrode at distance $\gamma$ is given by the well known Coulomb formula, for $\gamma$ considerably larger than the electrode dimensions. For elongated electrodes, the two-dimensional Coulomb formula can be used for intermediate distances that are large compared to a significant dimension of the cross section but small compared to the electrode length. The presence of the subject can be accounted for by the well-known method of images [27]. The field produced by a field electrode in its immediate vincinity can be calculated with simple models that are appropriate to the situation at hand, and are well known to those skilled in the art. Of course, these calculations need only be approximate or furnish reliable upper bounds of the field strength considered. Field calculations will be shown here for several field electrode configurations and settings of practical interest.

Presently, the experiments that underlie the invention will be discussed. The experiment setup used was much like the one shown in FIG. 1, with variations as to the skin area of predominant field application. The voltage applied between the field electrodes was usually a square wave with a frequency that can be manually tuned from 0.1 to 3 Hz. by adjusting the tuning control 21 on the generator 1 of FIG. 1; the voltage of the square wave was about 3 V. Frequencies at which a physiological effect occurs were found by manual frequency scanning. We needed a way to tell whether the nervous system of the subject was being affected by the external electric field. Invasive procedures were ruled out. Extensive EEG measurements were done on the scalp over appropriate points on the postcentral gyrus, using the method of averaging over many sweeps, in order to recover evoked potentials [13]. No evoked potentials showed up, even after averaging over 8000 sweeps, which brought the sensitivity to 100 nV. This showed that if anything is going on with the cutaneous nerves in the skin areas exposed to the field, it is not classical nerve stimulation. It was noticed that, at frequencies of about ½ Hz, the subject became drowsy and the EEG eventually showed increased amplitudes of slow waves, as judged by the signal waveform. The experiments need to be repeated, using hardware or software that provides for fast spectral analysis. Lacking this equipment, we looked for another indicator and found one in the form of ptosis of the eyelids.

When voluntary control of the eyelids is relinquished, the eyelid position is determined by the state of the autonomic nervous system. There are two ways in which this indicator may be used. In the first the subject simply relaxes control over the eyelids, and makes no effort to correct for any drooping. The more sensitive second method requires the subject to first close the eyes about half way. While holding this eyelid position, the subject rolls the eyes upward, while giving up voluntary control of the eyelids. With the eyeballs turned up, ptosis will decrease the amount of light admitted into the eyes, and with full ptosis the light is completely cut off. The second method is very sensitive because the pressure exerted on the eyeballs by partially closed eyelids increases parasympathetic activity. As a result the eyelid equilibrium position becomes labile, as evidence by a slight flutter. The labile state is sensitive to small shifts in the activities of the sympathetic and parasympathetic nervous system. The method works best when the subject is lying flat on the back and is viewing a blank wall that is dimly to moderately illuminated.

With this arrangement maximum ptosis occurred at a frequency near ½ Hz, with external electric field amplitudes on the skin ranging from 1 V/m to 25 V/m, where field amplitude is defined as half the peak-to-peak variation of the field strength. Immediately after onset, the ptosis frequency, defined as the frequency for maximum ptosis, slowly decreases until a steady frequency is reached in 5 to 10 minutes. It is believed that this is due to changes in the chemical environment of the resonating neural circuitry, caused by changes in the concentration of neurotransmitters or hormones that accompany or result from the resonance or from the subsequent shift in the autonomic nervous system state. The effect is here called "chemical detuning" of the ptosis frequency. The slow shift of ptosis frequency initially is so large that ptosis is lost if the frequency is not adjusted. The ptosis is accompanied by a state of deep relaxation, and a slight dull pressure at a spot about 1 cm above the point midway between the eyes.

As directly demonstrated by the ptosis experiments, the method of the present invention can be used for inducing relaxation in a subject. In further experiments with the device of FIG. 3 it has been found that, in a narrow range of frequencies around the ptosis frequency, the subject became very relaxed after a few minutes of field application, using peak field strengths on the subject's skin of about 1 V/m. The field was induced by field electrodes placed on the sides of the seat cushion of an easy chair. The ptosis frequency is higher in the evening than in the morning, just after awakening. For the subject tested, the evening ptosis frequency was 0.512 Hz at the onset, slowly shifting downwards to 0.465 Hz in about 10 minutes. Other autonomic responses can be obtained as well; tuning to a frequency of 0.540 Hz brings forth a tonic smile, provided that the subject gives up voluntary control of the facial muscles involved, so that the smile is controlled by the autonomic nervous system. Relaxation was experienced in the frequency range from 11% below to 4% above ptosis frequency. In the morning, the ptosis frequency at the onset was 0.490 Hz initially, shifting downwards to 0.460 Hz in about 7 minutes.

The method can also be used for the induction of sleep. Long-term tests running for about 400 nights were conducted on a subject who had trouble sleeping due to prolonged severe situational stress. In these tests, an external electric field was set up by applying a square-wave voltage of 20 V peak to peak between two field electrodes placed directly underneath the bed sheet on both sides of hips. Good results were obtained with frequencies of about ½ Hz. More recently, the device of FIG. 4 with a 3 V battery has been used successfully by the same subject for about 300 nights, under the same stressful conditions. Among the various electrode positions tried, the placement depicted in FIG. 1 was found to be most effective for inducing peaceful sleep. In this configuration the field electrodes 2 are located directly under the mattress, in the vertical mid plane through the longitudinal axis. The maximum electric field amplitude on the subject's skin is estimated as about 1 V/m. Two modes of operation were used. In the first mode, the unit was turned on at bedtime, at a frequency of 0.545 Hz, and thereafter left alone. After 15 minutes, the device automatically shifts the frequency upward by 3%, and turns off the oscillator after another 15 minutes. The subject usually fell asleep before automatic shutoff had occurred. A second mode of operation involves initial tuning for ptosis, followed by manual tracking of the slowly downshifting ptosis frequency, using the tuning control 21 shown in FIG. 1. About 5 minutes after a steady ptosis frequency is reached, the device is shut off manually. Tracking the ptosis frequency during its downward shift brings an increasingly deep state of relaxation and detachment. Sleep usually follows shortly after the device is shut off manually.

In regard to electrode placement there is a fundamental neurological difference between antisymmetric and symmetric excitation, in which the skin polarization is respectively antisymmetric and symmetric with respect to the midsagittal plane. In antisymmetric excitation, the weak fm signals from the modulated afferents act antisymmetrically on the brain. As a consequence, resulting resonances in neural circuits exhibit antisymmetry in left and right hemispheres, and the corpus callosum is "caught in the middle". In symmetric excitation, resonant modes occur synchronously in both hemispheres, and the corpus callosum is less involved, if at all. Experiments have shown that induction of sleep occurs with both excitations, but the symmetric excitation gives a somewhat softer feeling.

At frequencies somewhat different from the ptosis frequency, sexual arousal has been observed. In a male subject 67 years of age, the incidence of morning erections increased considerably when a square wave voltage was applied to field electrodes 2 placed as shown in FIG. 1, at a frequency of 0.563 Hz, and also, to a lesser extent, at a frequency of 0.506 Hz. These frequencies were found by manual scanning the range from 0.1 to 3 Hz. The signal generator of FIG. 3 was used, powered by a 3 V battery. For frequencies near 0.55 Hz, rather intense sexual excitement lasting for up to an hour has been induced in a male subject 70 years of age, by applying the external electric field predominantly to a skin area that includes the perinaeum skin.

Cutaneous receptors are particularly dense in glabrous skin, such as found on the palms of the hand, footsoles, areas of the genitals, nipples, areola, and lips. In the somatosensory map between areas of skin, the thalamus, and sensory cortex, the representation of these glabrous skin areas is greatly amplified. As a consequence, external electric field modulation of cutaneous nerves in glabrous skin is expected to excert a particularly strong effect on the central nervous system. We feel that this should be avoided by the general public; the effects are already ample when the field is applied predominantly to areas of the skin which are innervated sparsely, such as the thighs and the back. In particular, the lips should not be exposed strongly to the field, so that the areas of predominant application of the electric field by the general public should be away (say, at least 10 cm) from the head. Another reason for such choice is the avoidance of substantial polarization current densities in the brain, as discussed above.

Fixing experiment parameters except for the field strength, the described physiological effects are observed only for field intensities in an interval, called here "the effective intensity window". This feature of sensory resonances may be understood as due to nuisance-guarding neural circuitry that blocks impertinent repetitive sensory signals from higher processing. For the guarding circuitry to spring into action, the amplitude of the nuisance signal needs to exceed a certain threshold. This explains the upper boundary of the effective intensity window. The lower boundary of the window is due to the detection threshold of the sensory signals.

There needs to be concern about kindling [13, 18] of epileptic seizures in susceptable individuals. Kindling has traditionally involved the passage of electric currents of the order of 0.1 mA directly to a part of the brain, such as the amygdala. Although in the present invention substantial polarization current densities in the brain are avoided, an effect similar to kindling might occur if critical neural circuits are subjected to repeated sessions of periodic fm signals from somatosensory or visceral afferents. To guard against such an effect, the frequency of modulation of afferents for use by the general public should be chosen away from the frequencies involved in epileptic seizures. Modulation frequencies below 2 Hz appear to qualify in this regard.

The pathological oscillatory neural activity involved in epileptic seizures [13] is influenced by the chemical milieu of the neural circuitry involved, specifically through concentrations of GABA, glutamate, and aspartate [18], and perhaps β-endorphin. Since excitation of the ½ Hz sensory resonance may cause a shift in some of these neurotransmitter concentrations, the application of external electric fields may be useful for control and perhaps treatment of seizures. For this purpose, the patient wears compact field electrodes and a generator, to be manually activated upon experiencing a seizure precursor or aura. For patients with infrequent seizures, a small unit that contains the field electrodes as well as the generator, in the form of a small box, wallet, purse, or powderbox, may be particularly suitable.

The modulation of afferents by external electric fields may also be used for the control of tremors in Parkinson patients, by interfering with the underlying pathological oscillatory activity. According to Ref. [14], Scientific American of 1892 contains an article about controlling Parkinson symptoms by means of a vibrating helmet placed on the patient's head. For a 10 Hz vibration frequency, the subject is reported to experience, within a few minutes, a general lassitude and a tendency to sleep. Modulation of afferent nerves by a properly tuned periodic external electric field affords another and far less conspicuous excitation method, which is expected to have a similar result. The method of upsetting pathalogical oscillatory activity by applying an external electric field for modulating afferent nerves in skin areas away from the head may also be used for the control of seizures.

The method may be applied for the control of panic attacks, when these involve an abnormally high activity of the sympathetic nervous system. The experiments on ptosis, relaxation, and sleep show that the application of alternating external electric fields can diminish the activity of the sympathetic nervous system. The apparatus of FIG. 3 may be used, tuned to a frequency just below ptosis, or, for severe cases, right at ptosis. In this application it is convenient to use a generator and field electrodes mounted in a small single casing, such as a small box, wallet, purse, or the powder box of FIG. 7.

The question arises whether in the weak-field experiments discussed above the observed physiological effects are perhaps due to mechanisms other than the response of afferent nerves to the applied field. Candidates for such alternate mechanisms are polarization currents induced in the brain, and currents carried along high-conductivity paths provided by the cerebrospinal fluid, blood, and lymph, and subsequently detected by receptors. These alternate mechanisms are ruled out by experiments in which a sharply localized electric field is applied to the dorsum of the feet. The usual array of physiological responses was found in these experiments. It is therefore concluded that for weak aplied electric fields the observed physiological effects are indeed instigated by a response of afferent nerves to the external electric field.

The manipulation of the nervous system by external electric fields tuned to a sensory resonance frequency is subject to habituation, sensitization, classical conditioning, and the placebo effect. To minimize habituation in the use as a sleeping aid, the field should be predominantly applied to a different skin area each night. Sensitization, the placebo effect, and positive classical conditioning enhance the efficacy of the method. Clinical trials can be designed such that the placebo effect does not contribute to the statistical mean. This is done by arranging the generator output to the field electrodes to be passed or blocked by computer, according to a pseudo-random sequence with a seed that is changed from run to run, as determined for instance by date and time. Whether the field was on or off is unknown until the run is complete and the response of the subject has been entered into the computer. The arrangement is equivalent to a trully double-blind study.

The following considerations are important for proper design and use of the field generator, as well as for the planning and interpretation of experiments.

When an external electric field is applied to an isolated conductor, electric currents will flow that drive charges to the conductor surface. In steady state, these charges are distributed in such a way that the total electric field inside the conductor vanishes and the conductor surface is equipotential. These surface charges and electric currents are here called respectively "polarization charges" and "polarization currents". Although mainly used in the context of dielectrics, the wording is proper for isolated conductors as well.

Since the human body is a good conductor of electricity, exposure of an isolated subject to an alternating external electric field will cause polarization currents to flow broadly through the subject's body. The currents are of course accompanied by an ("internal") electric field, which turns out to be a very small fraction of the applied external field. In principle the polarization current and accompaning internal electric field may act on receptors, axons, synapses, and dendrites. As a purely electrical effect, the polarization current causes a polarization of the body, in which electric charges accumulate on the skin, if the latter is dry and the body is substantially insulated from its surroundings. The polarization charge density on the skin tracks the fluctuations in the applied external field. For an external electric field that varies as a square wave, the polarization currents flow only as brief pulses in response to the edges of the square wave. The polarization current pulses then have sharp leading edges, followed by an exponential decay with an e-folding time $$T_c = (\epsilon/\epsilon_o)\epsilon_o \eta, \quad (1)$$

where $\epsilon_o$ is the permittivity of free space ($8.85 \times 10^{-12}$ farads/m), $\epsilon/\epsilon_o$ the /average dielectric constant of the biological tissue, and $\eta$ the average resistivity. $T_c$ is called the charge relaxation time. Using the dielectric constant $\epsilon/\epsilon_o$ and resistivity $\eta$ for muscle tissue [16, FIG. 3—3], we find the estimate $$T_c = 710 \text{ ns}. \quad (2)$$

After each square wave edge, the current flow in the subject's body becomes negligibly small after a few times $T_c$. For square wave edges that are rounded with a rise time considerably larger than $T_c$, the polarization current pulses are broadened to the rise time of the edges. If spatial averages are used for the dielectric constant and resistivity, the charge relaxation time expressed by (1) is a spatial average. However, local relaxation times can differ substantially from the spatial average; for instance, the relaxation time of membranes ranges from 0.7 ms to 24 ms for the cases listed by Katz [17, table 1].

For external electric fields that vary slowly compared to the charge relaxation time (2), the polarization keeps up with the field. The resultant electric field, i.e., the sum of the applied field and the field due to polarization, is then essentially always perpendicular to the skin of the subject, and the electric field on the skin is proportional to the surface density of electric polarization in the skin. As will be discussed, experiments have shown that weak external field modulation of cutaneous nerves is due to electric polarization of the skin.

The polarization currents are subject to the skin effect [19, p. 5–85], in which the current density falls of exponentially, from the skin into the body, with e-folding distance $$\delta_s = \sqrt{(\eta/(\pi f \mu))}, \quad (3)$$

where $f$ is the frequency of the applied field, $\mu$ the permeability, and $\eta$ the resistivity of the body tissue. Calculation of the skin depth $\delta_s$ for the frequencies involved in the present invention gives values in excess of 1 m. It follows that the polarization current paths are not restricted by the skin effect.

The scale of the polarization current densities can be determined from the peak polarization current induced in the subject's body by the applied external field. This peak current can easily be calculated for the case that the applied electric field varies as a rounded square wave. The calculation is illustrated here for the field generator of FIG. 3. Let the resistors 13 and 14 and the potentiometer 12 all have the same resistance $R_o$, and let the potentiometer wiper be set at fraction $\alpha$ of the total resistance $R_o$. With a 3 V battery, the output voltage of timer 16 at point 15 is 2.5 V. Therefore, timer 6 produces a square wave with a voltage of $V_o=2.5$ V. A short calculation shows that the voltage between the two output terminals 11 swings from $\alpha V_o/3$ to $-\alpha V_o/3$, and that the output impedance, in the absence of output capacitor 22, is $$R_{out} = \alpha(3-2\alpha)R_o/3. \quad (4)$$

Hence, with an output capacitor $C_o$, the peak polarization current through the body of the subject is $$I_{max} = \left(\frac{C_{eb}}{C_0 + C_{eb} + C_{ee}}\right) \frac{2V_0}{(3-2\alpha)R_0}, \quad (5)$$

where $C_{eb}$ is the part of the capacitance between the field electrodes calculated from electrode charges at the end of electric field lines that go to the subject's body, and $C_{ee}$ is the remaining part of the capacitance between the field electrodes. Eq. (5) holds, provided that $R_O$ is much larger than the impedance of the subject's body, a condition that is satisfied in practice. The rise time of the external electric field is $$T_f = \frac{\alpha(3-2\alpha)}{3} R_0(C_0 + C_{eb} + C_{ee}), \quad (6)$$

provided that $T_f$ is much larger than the charge relaxation time (2) of the subject's body. This condition is satisfied in practice, unless $\alpha$ is very small. For the device of FIG. 3, with an output capacitor $C_O=1000$ pf, $R_O=1$ MΩ, $\alpha=1$, $V_O=2.5$ V, and the electrode configuration of FIG. 1, with the estimates $C_{eb}=1$ pf, $C_{ee}=1$ pf, the peak current $I_{max}$ of (5) becomes $$I_{max} = 5.0 \text{ nA}, \quad (7)$$

and the rise time $T_f$ of (6) is found to be $$T_f = 0.33 \text{ ms}. \quad (8)$$

Although these results were derived for the generator of FIG. 3, under the assumption that the timer produces a square wave with sharp edges, they will remain valid for rise times up to 100 ns. Comparison of the peak polarization current (7) with the 1 mA or so required for classical nerve stimulation [6,7] shows that the latter does not occur in the experiments under discussion. Estimating, for the setup of FIG. 1, the area of the skin that is subjected to appreciable field strengths as 2 A=600 cm², the peak polarization current density has over this area a spatial average $<j>=I_{max}/A$, which comes to $$<j>=17 \text{ pA/cm}^2. \quad (9)$$

Using η=400 Ohm cm as an average tissue resistivity [16, FIG. 3—3], the spatial averaged peak internal electric field strength $<E_i>$ that accompanies the average peak current density $<j>$ of (9) is $$<E_i>=6.8 \text{ nV/cm}, \quad (10)$$

for the case considered. These results are spatial averages of temporal peaks. In order to estimate the deviations from the average caused by nonuniformities in conductivity, consider a membrane with surface resistivity of 4000 Ohm cm² [17, table 1] subject to the perpendicular current density (9). The potential difference across the membrane is then perturbed by a mere 68 nV. Even if a factor 10 is used to account for the local nonuniformities in current density, the resulting peak membrane potential perturbation of 680 nV is about a factor 58000 below the membrane depolarization required for firing. This again shows that classical nerve stimulation does not occur. Since the applied field acts on the nerves, as evidenced by the observed physiological effects, the action must be a modulation of the spontaneous firing pattern of the nerve. The question remains whether the modulation is caused by the polarization currents or by the polarization charges on the skin.

In order to investigate this question, two experiments were performed. The field generator of FIG. 3 was used in both, with a 1000 pf output capacitor 22, $V_O$=2.5 V, and $R_O$=1 MΩ, where $R_O$ is the resistance of resistors 13 and 14, and potentiometer 12. The field electrodes were aluminum foil rectangles of 8×17 cm, placed over the upper skin of the subject's feet, with 1.5 cm insulation between the skin and the foils. The field electrodes were shielded on the outside with 8.5×20 cm rectangular pieces of grounded aluminum foil, separated from the field electrodes by a 0.5 cm thick layer of insulation. The subject's feet, fitted with the shielded field electrode assemblies, were placed in a 36×31×53 cm cardboard box, covered on the outside with grounded aluminum foil; the front opening of the box was shielded by a curtain of grounded insulated strips of aluminum foil. With this arrangement, the electric field was mainly confined to the 1.5 cm space between each field electrode and the opposing area of skin; any field spilling out from this space was essentially kept in the box by the grounded shield on the outside of the box and by the grounded curtain in front. The capacitance between the field electrodes via the subject's body is estimated as $C_{eb}$=11 pf, using a dielectric constant of 2.6 for the styrofoam insulation. The remaining capacitance between the field electrodes is estimated as $C_{ee}$=33 pf. With the output capacitor $C_O$=1000 pf, $V_O$=2.5 V and $R_O$=1 MΩ, Eq. (5) gives a peak polarization current of $I_{max}$=53 nA, multiplied by a factor that ranges from ⅓ to 1, as the intensity control potentiometer is advanced from small α to α=1. Full ptosis was observed with intensity control potentiometer settings from α=1 to α=0.06, at a frequency near 0.53 Hz.

Next, the experiment was repeated with one modification: the upper skin of the subject's feet, in the area opposite the field electrodes, was covered with a layer of conductive jelly, followed by a thin layer of overlapping strips of aluminum foil, and a thin insulating plastic sheet. In this arrangement, the polarization currents in the subject's body end up not on the subject's skin opposite the field electrodes, but on the aluminum foil covering of that skin area. The conductive jelly between skin and aluminum foil assures that the polarization charges make their way to the foil without delay beyond the charge relaxation time $T_c$ of (2). As a result, the polarization currents that flow in the subject's body are the same as in the previous experiment, but during the plateaus of the square wave, after a few times $T_c$, the skin is not subjected to an electric field. With intensity control settings α ranging from 1 down to 0.06, and tuning through the frequency range from 0.490 to 0.589 Hz, only very faint and fleeting ptosis was sporadically experienced for very short times; it could not be tracked in the usual manner by slowly tuning to lower frequencies. This result is to be compared with the full ptosis occurring in the previous experiment in which the feet were not covered with the highly conductive layer.

Varying the intensity control settings a in the two experiments gave pairs of settings in which the polarization current densities on the skin in the areas opposite the field electrodes is the same for the two experiments. For each of these pairs, the values of α are somewhat different, because the metal covering of the skin used in the second experiment extends to border areas for the purpose of capturing the edge field flux; therefore, the effective area of skin involved in the second experiment is slightly larger than in the first experiment. Considering the existence of these pairs of α settings for which the polarization current densities on the skin are the same for the two experiments, and the essential absence of ptosis in the second experiment, it is concluded that ptosis is essentially not caused by polarization currents in the skin. Moreover, settings with the same α give about the same polarization currents in the rest of the subject's body, away from the skin area opposite the field electrodes. It is therefore concluded that ptosis is essentially not due to stimulation or modulation of nerves other than cutaneous nerves, and it is not due to polarization currents in the brain either. It also follows that the ptosis is essentially not due to any stray electric field standing on the scalp or any other part of the skin other than the skin area lying directly across the field electrodes. It is concluded that the ptosis is essentially due to external electric field effects other than the polarization current, and that ptosis occurs essentially through cutaneous sensory nerves.

What are the effects of the external electric field, besides the polarization current? One such effect is the force exerted by the external field on hairs. However, experiments in which the field is exclusively applied to glabrous skin also give ptosis; hence, hairs are not involved in an essential way. The only possibility remaining is a shallow penetration of the external electric field into the subject's skin. Two such mechanisms have come to mind.

The first mechanism is due to thermal motion of the ions, that cause a smearing of the polarization charges through a Debye layer at the skin surface. The scale of such penetration in an electrolyte with monovalent ions of opposite charge is given by the Debye length [20]

$$\delta_d = \sqrt{\left(\frac{\epsilon}{2en} V_T\right)}, \quad (11)$$

where ε is the permittivity, e the elementary electric charge, n the concentration of one of the ion species deep in the electrolyte, and $V_T$=kT/e is the thermal voltage (26 mV at the normal skin temperature of 34° C.); k is the Boltzmann constant and T the absolute temperature. If the electrolyte is exposed to an external electric field $E_o$ perpendicular to its boundary, then at thermodynamic equilibrium the potential at depth z in the electrolyte is approximately $$V(z)=E_o\delta_d e^{-z/\delta_d}, \quad (12)$$

where $\delta_d$ is the Debye length given by (11), and the voltage is taken with respect to points deep in the electrolyte. The approximation (12) is good if $E_o\delta_d \ll V_T$. From (12) one has for the electric field $$E(z)=E_o e^{-z/\delta_d}. \quad (13)$$

These results are easily derived from balancing conduction and diffusion currents, together with the Poisson equation that relates the potential to the charge distribution. The calculation can be readily extended to the case of bivalent ions, and to mixtures of ions with different valences.

The above considerations for an electrolyte are applicable to the dermis, because of its considerable fluid content. But one may apply the theory also to the epidermis. This outer layer of the skin contains horny cells that suppress the mobility of ions. However, the relation between mobility and diffusivity of ions is still given by the Einstein relation. Therefore, the equilibrium thermodynamics of ions in the epidermis is the same as in an electrolyte. Since the ion concentration in the epidermis is relatively small, the Debye length is relatively large; for example, for an ion density of $10^7$ per $cm^3$ and a dielectric constant of 4, the Debye length (11) is 0.54 mm. Sensory receptors in dermal papilla that protrude into the base of the epidermis are then subjected to the remnant of the electric field as it penetrates from the outside, in the manner shown by Eq. (13). If the cytoplasm of the receptor is at the same potential as the deep body tissue, then the membrane potential at the tip of the receptor is perturbed by the about the voltage (12), using for z the thickness of the epidermis. Taking 0.2 mm for that thickness, and parameters of the epidermis as in the above example, an external field of 1 V/m on the skin is found to perturb the membrane potential of the receptor tip by about 0.4 mV.

Such a change in membrane potential is much too small to fire the nerve. However, as pointed out by Terzuolo and Bullock in a classical paper [25], modulation of the frequency of an already active neuron can be achieved with voltages very much lower than those needed for the excitation of a quiet neuron. Voltage gradients as small as 1 V/m across the soma were sufficient to cause a marked change of firing of adaptive stretch receptors of crayfish [25]. Terzuolo and Bullock further remark [25] that the value of the critical voltage gradient for this effect may actually be much smaller than 1 V/m. The 0.4 mV membrane voltage perturbation calculated above for the example may be sufficient to cause frequency modulation of the firing pattern of the receptors investigated by Terzuolo and Bullock. Perhaps the same behavior occurs for other slowly adapting mechanoreceptors that exhibit spontaneous firing, such as Ruffini endings and Merkel cells, which are found roughly at a depth of 0.2 mm in the skin [21, 23, 34].

A second mechanism for penetration of the external field into the epidermis is provided by sweat ducts. These narrow ducts are normally kept at least partially filled by the sweat glands and capillary action. The highly conducting thin sweat column in the duct will be polarized by the external electric field. As a result the field will be severely distorted, causing the equipotential surfaces to crowd together near the tips of the columns, and dip deep into the epidermis in between the sweat ducts. As a result, a local field that is a small fraction of the external field $E_O$ acts on cutaneous receptors which lie in papilla that protrude into the base of the epidermis. The associated potential must be added to that due to the first mechanism.

Cold receptors also lie at shallow depths [22] and exhibit spontaneous firing, so that they need to be considered as candidates for modulation by externally applied weak electric fields. Therefore, an experiment was performed in which steady electric fields of up to 1 KV/m were applied to the skin. If modulation occurs, these electric fields may induce a sensation of skin temperature change. No such sensation was experienced. However, there may have been rapid adaption to the electric field stimulus, and the effect of the field on the firing pattern of cold receptors may differ in nature from the pattern change due to temperature. The latter possibility is suggested by the complicated coding of temperature information, which is much more intricate than mere frequency modulation [26]. Therefore, the observed absence of a temperature sensation in steady-state electric field application does not quite rule out modulation of cold receptors by the applied external electric field.

There have been further developments, as follows.

It has been observed that lower field strengths suffice for the excitation of sensory resonances when the skin area of dominant field application is increased. This "bulk" effect is important for the proper use of the invention, and can be understood as follows. The field causes a frequency modulation of the stochastic firing of the affected afferent fibers. If these fibers synapse, either directly or indirectly, upon a summing neuron, then the sequence of current injection spikes into the dendrite of the neuron will be a slightly modulated Poisson stream. For zero modulation a Poisson distribution is expected on theoretical grounds if the number N of synapsing afferents is large, since the afferent spike trains add and interlace. This results in a high-frequency sequence of charge injections, in which the features of the individual afferent spike trains are substantially washed out, in much the same way as density nonuniformities of a substance suspended in a fluid are removed by stirring. The Poisson distribution is found to be a good approximation in computer simulations with N of the order of 4000, substantially independent of the details of the firing probability distributions for the individual afferents. As a consequence of the Poisson distribution, the variance as well as the mean of the number of injection spikes into the summing neuron that occurs in a fixed time interval $\Delta t$ is $$\lambda = Nf_O\Delta t, \quad (14)$$

where $f_O$ is the average frequency of the afferent spike train, assumed to be the same in each afferent, for simplicity. For large N the excitatory synaptic current needs to be balanced with an inhibitory current, lest the integrated signal by far exceeds the firing threshold and the summing neuron is locked into a maximal firing state. The balance requires that, in addition to N excitatory neurons, roughly N inhibitory neurons also synapse on the summing neuron. The inhibitory current spikes contribute to the noise, thus increasing the variance by about a factor 2. Balanced excitatory and inhibitory activity has been recently considered as a mechanism for rendering cortical neurons sensitive to small fluctuations in their synaptic current; see [35] and the references contained therein. With modulation present, the Poisson distribution still stands short-term, but $\lambda$ has now a slow sinusoidal variation with the frequency of the applied electric field. All modulated afferents contribute coherently to this sine wave. As a result, the signal-to-noise ratio of the fm signal that is present in the temporal density of the current injection spikes is proportional to $mNf_o/\sqrt{(2f_oN)}=m\sqrt{(f_oN/2)}$, where m is the depth of the frequency modulation. The latter is expected to be proportional to the applied external field amplitude E. Hence, one expects the signal-to-noise ratio to be proportional to $E\sqrt{(f_oN)}$. The fm signal is somehow demodulated by subsequent neural circuitry. The latter contains or is followed by nuisance-guarding circuits, with the result that the observable response to the field application exhibits an effective intensity window. One expects the ultimate response to be a function of the signal-to-noise ratio of the current injections into the summing neuron, so that $$\text{observable response} = \text{function of } (E\sqrt{(f_oN)}). \quad (15)$$

Eq. (15) shows the bulk effect. For excitation of sensory resonances through modulation of cutaneous nerves, N is roughly proportional to the skin area $A_s$ over which the field is predominantly applied, and also to the surface density ρ of the affected nerves, so that in (15) one has $$N = c\rho A_s, \quad (16)$$

where c is a constant. If the fm detection circuitry receives inputs from M similar summing neurons, the results (15) and (16) still hold if N is replaced by MN. Very shallow frequency modulation can be detected amidst the large fluctuations occurring in the spontaneous firing of the individual afferents, if the product MN is large. This result is helpful in understanding the exquisite sensitivity of the human electroception observed and discussed here. Stochastic resonance [33] perhaps contributes to the sensitivity as well.

The peak value (10) of the internal electric field induced by an external field of 1 V/m with rounded square wave time dependence at a frequency near ½ Hz shows that the internal field is a very small fraction of the external field. The same conclusion holds for sinusoidal fields, for which the internal field is easily found to be $$E_i = 2\pi f T_c E_o, \quad (17)$$

where $T_c$ is the relaxation time (1), $f$ the field frequency, and $E_O$ the external electric field. For $f=½$ Hz, and the value $T_c$ given by (2), Eq. (17) gives for the internal electric field $$E_i = 2.2 \times 10^{-6} E_o. \quad (18)$$

It follows that, for the purpose of calculating the field induced on the skin by field electrodes, the internal electric field may be neglected, so that the subject's skin is an equipotential surface. For the configuration of FIG. 2, the skin voltage is then determined by a capacitive voltage divider with two capacitors, one formed by the left electrode 2 and the apposing skin area 36', and the other formed by the right electrode 2 and the skin area 36. If both electrodes are placed opposite the skin by a small separation d, the electric field on the skin in the areas 36 and 36' is approximately $$E = V/2d, \quad (19)$$

where V is the voltage applied between the field electrodes.

For many applications as well as for research purposes it is convenient to use as field electrodes a doublet, because it is compact and its field can be easily calculated for several practical settings. Referring to FIG. 8, the doublet consists of two field electrodes 50 and 51 of identical size and shape placed parallel and in registration with each other, and separated by a dielectric layer 52 such as to form a parallel-plate condensor. The dielectric may just be air. Optionally, insulating sheets 53 may be applied to the outside surfaces of the field electrodes 50 and 51, so that the electrodes, the dielectric layer and the insulating sheets form a sandwich of five layers that are alternatingly insulating and conductive. The dielectric and insulating sheets have a slight overlap with respect to the field electrodes in order to provide effective insulation. Application of a voltage between the field electrodes causes charging of the doublet, so that electric charges of opposite sign accumulate on the electrodes. If the applied voltage fluctuates in time, so will the electric charge on the electrodes.

The field electrodes of the doublet are connected via conductors 54 to an input port 55 for receiving a fluctuating voltage difference. This connection is straightforward for the single doublet of FIG. 8, but for multiple doublets more complicated connections may be desired, and voltage dividers may be used as well. Such connections and voltage dividers are provided by a distributor which charges the doublets, upon receiving a fluctuating voltage at the input port. Examples for distributors for multiple doublets are shown in FIGS. 9 and 10, to be discussed. The straightforward connections for the single doublet of FIG. 8 are seen as a special case of a distributor.

In FIG. 8, the doublet formed by the sandwich of conductive foils and insulating sheets has a plane shape, but the doublet may be curved or flexible, such as to fit body contours.

Figure 11:
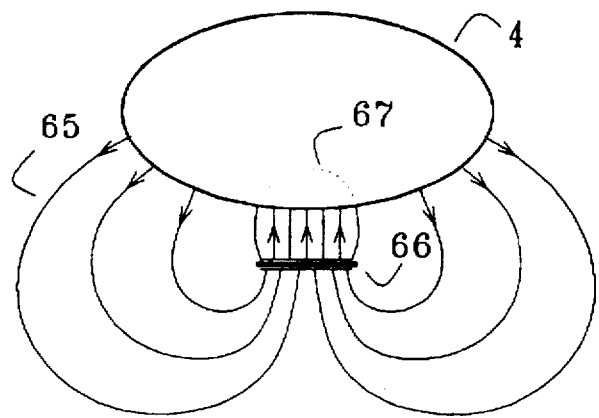
FIG. 11 illustrates the electric field of a doublet placed near a subject.

Upon charging the doublet, a concentrated field arises between the field electrodes; the condenser action is mainly due to this field. A much weaker field occurs in the space outside the parallel-plate condenser, this space being defined as the set of points P through which no straight line exists that intersects the two field electrodes at points that are on opposite sides of P. This "fringe field" is not essential for the condenser action, but in the present invention it is used as the electric field to which the subject is exposed. An example configuration of doublet and subject is shown in FIG. 11, where the doublet 66 is placed near the subject 4, such as to apply the fringe field predominantly to region 67 of the skin. The fringe field of a charged doublet in the presence of the subject is illustrated by several field lines, such as 65. In FIG. 11 the doublet is oriented parallel to the nearby skin, but other orientations may be used.

At this point the difference with Brennan [11] should be noted. In that patent at least part of the subject's brain region is located between the pair of electrodes. In contrast, in our doublet the space between the field electrodes is narrow and occupied only by one or more dielectric layers; the subject is not exposed to the field between the electrodes, but to the fringe field, as illustrated in FIG. 11. For the doublet, the difference with the Brennan patent remains even if the skin area of predominant application of the fringe field is on the head or close to the head. The condition of avoiding substantial polarization current densities in the brain can be met by limiting the peak external field amplitude on the head such that the scale of the polarization density is below 70 fA/cm$^2$. With this condition satisfied, the external electric field will still modulate cutaneous nerves in the scalp.

Experiments have been done with a doublet placed about 10 cm from the top of the head in an orientation parallel to the local skin. The doublet that has 45×70 mm field electrodes, was contained in a small box that also contained a generator for producing a near-sinusoidal voltage with 3 V amplitude and a tunable frequency in the range from 0.43 to 0.58 Hz. Use of this setup as a sleeping aid over a period of about a month has been very successful.

At distances γ large compared with the doublet dimensions, the fringe field of a doublet plus the charge displaced in the dielectric is a dipole field with as source strength the electric dipole moment Qδ, where Q is the charge on one of the electrodes of the doublet, and δ is the electrode separation. Using the standard approximation for the capacitance of a parallel-plate condensor one finds $\epsilon_o VA$ for the dipole moment, where $\epsilon_o$ is the vacuum. At distances γ that are large compared to the doublet dimensions, the dipole field in free space has the magnitude $$E = b \frac{AV}{4\pi r^3}, \tag{20}$$

where A is the electrode area, and V the voltage applied between the two electrodes of the doublet. The factor b is $$b = \sqrt{(1 + 3\cos^2\theta)}, \tag{21}$$

where θ is the polar angle with respect to the normal to the electrode surface, as seen from the point where the field is considered. Eq. (20) is a good approximation if the electrode dimensions and separation are small compared to the distance γ.

For the special case that the electrodes of the doublet are flat circular discs of radius R, the fringe field on the rotational symmetry axis can be calculated exactly in the limit of zero electrode separation. In this limit the dipole moment density on the circular disc is uniform and equal to $\epsilon_o V$, and the field on the axis is found to be $$E = (\tfrac{1}{2})VR^2/(R^2+z^2)^{3/2}, \tag{22}$$

where z is the distance to the doublet. Eq. (22) expresses the field in free space. Presence of a subject near the charged doublet causes the field to be influenced by polarization charges induced on the subject's skin by the field. If the doublet is small compared with the subject and is positioned parallel to the nearby skin at a distance d that is small compared with the dimensions of the subject, as in FIG. 11, the field at the intersection of the doublet axis and the skin is approximately $$E = VR^2/(R^2+d^2)^{3/2}, \tag{23}$$

as follows readily with the method of image charges [27], when the skin near the doublet may be approximated as flat. For very small or zero distance d one then finds for the central field $$E = V/R, \tag{24}$$

showing that, counter to intuition, the field does not become large for small d. That is because for small d the subject's skin is at nearly the same potential as the doublet electrode nearest the skin, by the action of the capacitive voltage divider involved.

Figure 12:
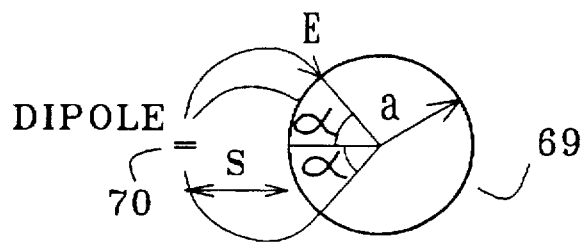
FIG. 12 provides information for estimating the polarization current and the maximum electric field induced on the subject's skin by a doublet.
Figure 12:
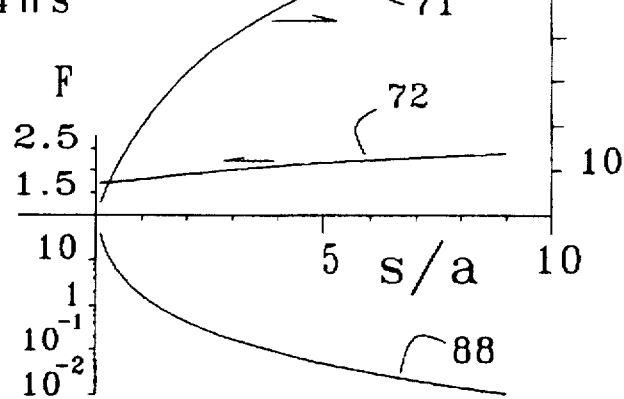

The approximation (23) is inadequate for doublets placed at a distance from the subject that is considerably larger than the doublet size. The field due to the polarization charges on the subject's skin can then be estimated with the image charge method by representing the subject's body as a conductive sphere. With this crude model one can calculate a correction factor F for the maximum field on the subject's body. FIG. 12 illustrates the model for the case that the doublet is placed a distance s from the subject, with the electrodes oriented parallel to the line of shortest distance between doublet and subject. The subject is modelled as a conductive sphere 69 with radius α. The doublet 70 causes electric polarization of the sphere, such that on the sphere the total electric field is perpendicular to the spherical surface. The maximum electric field on the sphere can be expressed as $$E_{max} = F \frac{AV}{4\pi s^3}, \tag{25}$$

where the factor F is read from graph 72. The angle α at which the field on the sphere is maximum can be read from graph 71. The graphs 71 and 72 were calculated with the method of images [27].

For this model one can also calculate the capacitance C between the doublet and the sphere. This capacitance determines the total polarization charge Q on the upper half sphere of FIG. 12, that occurs in response to a voltage V applied to the doublet, $$Q = CV. \tag{26}$$

The capacitance can be determined from $$C = gA/\alpha, \tag{27}$$

where the factor g can be read from graph 88 of FIG. 12. For a sinusoidal field with frequency $f$, the amplitude of the total polarization current induced in the sphere is $$I = 2\pi f Q. \tag{28}$$

Eqs. (27) and (28) provide estimates for the total polarization charge induced on the skin of the subject by a nearby doublet, and the total polarization current induced in the subject's body. These results are valid for the case that the plane of the doublet is oriented parallel to the shortest line between doublet and subject, as in FIG. 12. Similar calculations can easily be done for other orientations.

In certain experiments and clinical applications there is a need for an external electric field that is strictly confined to two selected skin regions. Such a field can be set up with a shielded electrode pair as depicted in FIG. 10, where field electrodes 2 and 2' of identical shape and size are closely apposed, in parallel fashion, respectively by electrodes 38 and 39 called shield electrodes. The latter have the same size and shape as the field electrodes 2 and 2', and are positioned and oriented such as to bring their contours in registration with those of the corresponding electrodes 2 and 2'. Furthermore, a conductor 40 connects the shield electrodes, so that they have the same potential. Electrodes 2 and 2' are connected by wires 41 to the input port 55 which is to receive a voltage from the generator. With the generator voltage applied to the input port 55, the voltage on the field electrodes 2 and 2' is respectively $V_1$ and $V_2$. Although not shown, insulation is applied between electrodes 2 and 38, and between electrodes 2' and 39. Optionally, insulation is applied to the top and bottom of the two resulting structures as well, resulting in two 5-layer sandwiches. The latter are positioned in close proximity of the skin 37 of the subject, in the orientation shown in FIG. 10. If the sandwiches are placed parallel and at equal distances to the skin 37, then both the skin and the shield electrodes have the potential $(V_1+V_2)/2$, so that no field lines stand between the shield electrodes 38 or 39 and the subject. It follows that the external electric field is then confined to four narrow spaces, viz., the space between electrode 2 and the skin 37, between electrode 2' and the skin, between electrode 2 and the shield electrodes 38, and between electrode 2' and shield electrode 39, except for edge fields pouring from the edges of the narrow spaces. These edge fields extend over a distance of the order of the electrode separation or the distance from electrode 2 or 2' to the skin. If these separations are very small, so will be the spatial extents of the edge fields, and the external field on the skin then will be essentially confined to the skin areas directly apposed by the electrodes 2 and 2'. Electrodes 2 and 2' need not be positioned in close proximity to each other.

In the foregoing discussion the field electrodes 2 and 2' were assumed to have the same shape, size, and distance to the skin. One can deviate from these conditions by making adjustments in the distances at which the shield electrodes are applied over the field electrodes 2 and 2', such as to assure that the shield electrodes are at the same potential as the skin. The shield electrodes 38 and 39 may be conductive foils or conductive meshes. The conductor 40 may be a conductive foil, which may simply be the continuation of the shield electrodes 38 and 39. If the field electrodes 2 and 2' are deployed at a short distance from each other, the shield electrodes 38 and 39, together with the conductor 40 may be implemented as a single conductive foil.

The shielded electrode pair of FIG. 10 can be seen as two doublets with opposite electric dipole moment that are connected in series, and therefore as a special case of doublets with a distributor as discussed above. In this case the distributor comprises the input port 55, the connections 41 between the field electrodes and the input port 55, as well as the connection 40 between the shield electrodes 38 and 39.

A well-designed and deployed shielded pair of field electrodes limits the field application essentially to the skin area directly apposing the field electrodes. Therefore, the shielded pair can be used on skin areas very close to the head, without causing substantial polarization currents in the brain. An important example of such deployment is localized field application to the skin overlying the vagus nerve in the neck.

A doublet may be used also in the compact configuration wherein the field electrodes are contained together with the generator in a single casing, such as a small electronic project box, or the powder box of FIG. 7. The distant fringe field can be further increased by placing a conductor in front or behind the doublet. The conductor will then be polarized, and the electric dipole formed by the polarization charges will boost the distant field. A particularly effective conductor for this purpose is shown in FIG. 13. There, the doublet 42 is apposed, at a short distance d, by a conductive foil 46 of the same shape, size, and orientation as the electrodes of the doublet. Another such conductive foil 47 is placed at a distance S, parallel to foil 46, and the two foils 46 and 47 are connected by a conductor 48. The conductor comprised of 46, 47, and 48 is polarized by the fringe field that emanates from the doublet, so that foils 46 and 47 acquire opposite polarization charges of magnitude Q, thereby forming an electric dipole with moment QS. The orientation of this induced dipole is the same as that of the doublet. Hence, the foils 46, 47, the wire 48 may be seen as a "passive doublet", which boosts the distant electric field. The boost factor us the same in all directions. For doublets of circular shape, a short calculation that uses Eq. (24) gives the result that the total electric dipole moment, and therefore the distant field, is increased by at least a factor S/R+1, as compared with the field of the original dipole by itself. It is readily seen that the same result is obtained whether the passive doublet is placed in front or behind the doublet i.e., in FIG. 13, respectively below or above doublet 42. In FIG. 13, the passive doublet should however not be placed on the left or right of doublet 42, since then the dipole moment induced in the passive doublet would have a direction opposite the dipole moment of doublet 42, so that at large distances the electric field would be reduced rather than boosted. The space between the foils 46 and 47 may be put to good use by placing the generator there, so that a compact package results that can be contained in a single small casing, similar to the one shown in FIG. 7. In spite of its small size, such a device can generate an adequate field at considerable distance from the subject, because of the electric dipole moment boost by the passive doublet.

There sometimes is a need for a short-range electric field that is produced by field electrodes placed some distance away from the subject's body. This can be accomplished with an assembly of doublets designed such that their combined field is asymptotically multipole, i.e., at large distances $\gamma$, the potential falls off as $1/\gamma^k$, with $k>2$. The integer k is called the order of the multipole. Such an assembly of doublets is here called a multipole field electrode. For an assembly of doublets to be a multipole electrode, certain conditions need to be satisfied. These conditions are here discussed for an assembly of doublets that is axisymmetric and lies in a plane. The produced electric field is then axisymmetric as well, with symmetry axis, say, z. In free space the potential for such a field has a so-called multipole expansion [28] with terms of the order of $1/\gamma^2$, $1/\gamma^4$, $1/\gamma^6$, etc. The coefficients of these terms depend on the radii and driving voltages of the m individual doublets that make up the assembly. The radii and driving voltages can be chosen such that the first m−1 terms in the multipole expansion vanish. The leading term of the expansion is then of the order $1/\gamma^{2m}$, so that the field produced by the assembly is asymptotically multipole of order 2m. The details of the calculation are not shown here, but can be easily derived by those skilled in the art. The result of the calculation is as follows.

Consider, in a plane, an assembly of m concentric circular electric doublets, with radii $R_j$, and voltages $V_j$, j=1 to m. The first m−1 terms in the multipole expansion of the electric potential produced by the assembly vanish if $$\Sigma R_j^2 V_j = 0, \Sigma R_j^4 V_j = 0, \ldots \Sigma R_j^{2m-2} V_j = 0, \tag{29}$$

with the sums taken over j=1 to m. This is a Van der Monde system [29] that can be solved, for any m, by a modification of the Pascal triangle for the binomial coefficients. The modification entails starting each row of the triangle with the row number, and completing the row by the well-known Pascal triangle construction. One thus finds for the first row 1, for the second row 2,1, for the third row 3,3,1, for the fourth row 4,6,4,1, etc. For the assembly of m doublets, the modified Pascal triangle must be completed up to row m. The voltages $V_j$ are then to be taken proportional to the sequence of numbers in the mth row of the triangle, with alternating signs. The squared radii, $R_j^2$, of the individual doublet discs are to be taken proportional to the index j. The resulting $V_j$ and $R_j$ satisfy Eq. (29), as can be verified by substitution. The superposition of m doublet discs can be implemented in practice by adding the voltages in the regions of overlap, and applying these sums as driving voltages to annular doublets with radii $R_{j-1}$ and $R_j$, $R_o$ being chosen as zero. As an example for m=4, one has a central doublet disc of radius R driven by a voltage V, an annular doublet with inner radius R and outer radius R√2 driven by the voltage −3 V, an annular doublet with inner radius R√2 and outer radius R√3 driven by a voltage 3 V, and an annular doublet with inner radius R√3 and outer radius 2 R driven by the voltage -V. In practice the voltages are derived from an accurate resistive divider. The above calculations give a good approximation if the electrode separations in the individual doublets are very small compared to the distance γ, so that the fraction of the areas of the electrodes that have considerable nonuniformities in charge distribution is negligible. If the order of the multipole field electrode is increased, the asymptotic multipole field falls off faster, the central lobe narrows, and a larger driving voltage is required in order to maintain the same field strength at any far fixed point on the symmetry axis. Furthermore, finer fabrication tolerances are required, because the multipole action is based on the cancellation of the lower order pole contributions. The latter two effects place a practical upper limit on the order of the multipole field electrode.

The field of a charged doublet polarizes the adjacent doublets. This cross coupling is unwanted, since it complicates design of the multipole field electrode. The coupling can be kept to negligible levels by choosing the distance between the two field electrodes of each doublet very small.

The structure of the multipole electrode of order 8 of the type discussed above is shown in FIG. 9, as an axisymmetric assembly of individual doublets 57, 58, 59, and 60 with symmetry axis 56. The doublet 57 has the shape of a disc, whereas the doublets 58, 59, and 60 have annular shape. The assembly of doublets is fastened to two adhesive sheets of insulation 61, which are stuck together in the border region 62. An insulating layer 66 is applied between the upper assembly consisting of the doublets 57 and 59, and the lower assembly consisting of the doublets 58 and 60. Each of the doublets consists of two field electrodes, such as 63 and 64 for doublet 57, insulated by a dielectric layer 65. Here, the distributor involves a resistive voltage divider 68 and connections to the various points in the doublet assembly and to the input port 55 that is to receive a fluctuating voltage. For readability of the drawing, some of these connections are implicitly indicated as pairs of identical letters placed at certain connection points; such point pairs are understood to be electrically connected.

The multipole electrode of FIG. 9 has four doublets which together cover a geometric disc without leaving gaps. However, configurations with gaps can be designed, by considering each gap as an annular doublet with zero driving voltage. The coefficients $R_j^2$, $R_j^4$, etc. in Eq. (29) are then replaced by differences of powers of the outer and inner radii of the annular gaps, as will be evident by carrying out the multipole expansion of the electric potential. The solution by the modified Pascal triangle no longer holds, but the resulting equations that express the vanishing of the first m−1 terms in the multipole expansion can be readily solved numerically. Non-axisymmetric electric multipoles can be designed as well, but the analysis then requires spherical harmonics [28].

A multipole field electrode of order 8 has been built as a circular planar sheet, with a central doublet of R=6.25 cm radius. In free space, the asymptotic field has a central lobe with polar angle of 18.2°, and the electric field on the symmetry axis, at distance z from the plane of the multipole sheet, is calculated as $17.5 \text{ V}(R/z)^9$ V/m, where V is the driving voltage on the assembly, in volts. When the multipole is placed near an isolated subject, the polarization charges on the subject's skin modify the field, such as to render it perpendicular to the skin. The field modification can be estimated with the image charge method by modeling the subject as a conductive sphere. In an application as a sleeping aid, the 8th order planar multipole field electrode described above was placed under the mattress of the subject. The external field at the point P of intersection of the multipole axis with the skin was calculated to be a factor 2.54 times the free field value, using z=13 cm, and a radius α=24 cm for the conductive sphere radius in the model. Using a rounded square wave generator with a peak to peak voltage of 6 V connected to the input port (55 of FIG. 9) of the distributor, the total external field at point P is calculated as 183 mV/m.

The multipole field electrode produces a field with a lobe structure, so that on the subject's skin there is a set of zones of positive and negative field amplitudes. In order to discuss these field zones somewhat quantitatively, it is convenient to use a model in which the skin lies in a plane, so that the polarization effects can be expressed by a simple version of image charges [27]. If the multipole symmetry axis is perpendicular to the plane, the field zones are bounded by concentric circles centered at point P. On these circles the field vanishes, and the field changes sign when crossing the circles. For the deployment described above these circles are centered at point P and have the radii 3.6, 7.8, 11.0, and 12.8 cm, as follows from a calculation of the multipole field in the vincinity of a conductive plane. On the plane, the maximum field amplitude occurs at point P. Going from P through the concentric zones gives for the field extrema the sequence −0.18, 0.015, −0.00017, and $5 \times 10^{-7}$, all relative to the amplitude at P. The sequence of extrema shows that the field falls off very fast indeed. Similar features will occur in reality, where the shape of the skin deviates from a plane at larger distances to point P as contact with the mattress is lost. The small size of the central zone and the existence of field zones of alternating field direction have important consequences.

First, the small size of central zone affords a sharply localized field application, in spite of the fact that the multipole field electrode is some distance (here 13 cm) away from the subject. For example, this is useful in sexual excitation, which can be arranged by the subject by taking a position on the mattress such that the central lobe of the multipole field electrode under the mattress is aimed at the perinaeum.

Second, the modulation of cutaneous nerves in adjacent zones is 180° out of phase. The same is true for the fm signals received in corresponding zones of the thalamus, by virtue of the somatotopic map of the cutaneous sensory system. The resulting fine spatial scale of the signal structure into the thalamus is expected to have consequences for the excitation of sensory resonances.

The setup with the multipole field electrode placed under the mattress at lumbar level has been tested as a sleeping aid for about 30 nights, with good results.

The main lobe of the multipole field electrode may be aimed at a skin region on the head or close to the head, as long as the brain is not exposed to substantial polarization current densities. This condition can be met by limiting the peak amplitude of the external field on the skin. The field can still excite sensory resonances, by virtue of the presence of cutaneous nerves in the skin of the head, including the scalp.

A new sensory resonance has been found near 2.4 Hz. The resonance shows up as a sharp increase in the time of silently counting backward from 100 to 70, as fast as possible, with the eyes closed. The counting is done with the "silent voice" which involves motor activation of the larynx appropriate to the numbers to be uttered, but without the passage of air, or movement of mouth muscles. The motor activation causes a feedback in the form of a visceral stress sensation in the larynx. Counting with the silent voice must be distinguished from merely thinking of the numbers, which does not produce a stress sensation, and is not a sensitive detector of the resonance. The larynx stress feedback constitutes a visceral input into the brain and thus may influence the amplitude of the resonance. This unwanted influence is kept to a minimum by using the count sparingly in experiment runs. The protocol adapted in our laboratory, after extensive trial and error, is to have experiment runs of 40 minutes duration, with counts taken at times 0, 20, and 40 minutes into the run. In early experiments the count was done from 100 to 70, but as experience was gained, we switched to the more sensitive 100–60 counts. Since counting is a cortical process, the 2.4 Hz resonance is here called a cortical sensory resonance, in distinction to the autonomic resonance that occurs near ½ Hz. In addition to affecting the silent counting, the 2.4 Hz resonance is expected to influence some other cortical processes as well. It was found that in the long run the resonance has a sleep inducing effect. Very long exposures cause dizziness. The frequency of 2.4 Hz raises concerns about kindling; therefore, the general public should not use the 2.4 Hz resonance until this concern has been addressed properly in experiments.

The sensitivity and numerical nature of the silent count makes it a very suitable detector of sensory resonance, thereby affording several experiments which clarify somewhat the processes involved, and provide guidance for the proper use of the invention.

First, the experiment aimed at resolving the question whether it are the polarization currents or the polarization charges that cause the excitation of the ½ Hz autonomic resonance has been repeated for the 2.4 Hz cortical resonance, using the same field strengths applied in the same manner to the same areas of skin, but with a sine wave instead of a rounded square wave. The amplitude of the voltage applied to the field electrodes was 1.45 V, resulting in an external electric field at the skin with a maximum amplitude of 48 V/m. A frequency of 2.407 Hz was used, and the counts were done from 100 to 60. As for the ½ Hz experiments discussed, the electric field was applied to the dorsum of the feet in a localized manner. In the first experiment the silent counts were 37 s at the start t=0 of the run, 53 s at t=20 minutes, and 75 s at t=40 minutes, the end of the run. The pronounced increase of counting time shows excitation of the 2.4 Hz resonance. In the second experiment the conditions and parameters were the same, except that the skin of the dorsum of the feet was covered with conductive jelly and aluminum foil, all insulated from the field electrodes. This arrangement removes the polarization charges from the skin, whereas the polarization currents in the skin and the body are the same as before. The counts were 32 s at t=0, 34 s at t=20 minutes, and 33 s at t=40 minutes, so that the resonance was not excited. Comparison of the two experiments shows that the excitation of the resonance is not due to polarization currents, but rather to polarization charges on the skin, in agreement with the conclusion reached above for the ½ Hz autonomic resonance experiments.

The magnitude of the polarization current densities in the subject is calculated as follows. With an estimated 11 pf capacitance between the field electrodes via the subject's body, the polarization current amplitude comes to 241 pA. Assuming that this current is spread over a skin area that is 10% larger than the area of the nearby field electrode, the maximum current density in the subject's body is found to be 1.6 pA/cm$^2$. The experiment shows that such a small current density applied to cutaneous nerves in the dorsum of the foot is not capable of exciting the 2.4 Hz resonance, but the accompanying polarization charges can.

In the described experiments the polarization current through the skin is concentrated in the skin area S immediately apposing the field electrodes, fanning out from there into deeper lying tissue. A similar current distribution can be set up by means of contact electrodes attached to the skin in the area S. This affords another check on the conclusion that the resonance is not excited by the currents, in the parameter range considered. To perform this check, the output of the sinusoidal voltage generator was connected to the contact electrodes via a small capacitor which at the low frequencies presents an impedance very much larger than that of the subject's body. The generator thereby becomes effectively a current source. The two contact electrodes had the same size and shape as the field electrodes in the field experiments described above, and each was attached to the dorsum of the foot through a layer of conductive jelly. Passing in this manner a sinusoidal current with an amplitude of 48 nA at 2.417 Hz gave rise to a 100–60 count of 35 s at t=0, 36 s at t=20 minutes, and 34 s at t=40 minutes, showing that the resonance was not excited. The maximum current density in the skin was 321 pA/cm$^2$, considerably larger than in the field application discussed. Yet, the current did not cause excitation of the 2.4 Hz resonance. It may be remarked that the current density of 321 pA/cm$^2$ perhaps falls outside the effective intensity window, but that is not the case, as follows from the next experiment discussed.

Thus far arrangements have been discussed where the modulation of afferents by the field occurs in the receptors of afferent fibers. An essentially different situation of interest occurs when the tissue underlying the skin area of predominant field application is traversed by a nerve that has no receptors in the skin area. The question then arises whether the spike trains carried by the afferent fibers in the nerve can be modulated without causing classical nerve stimulation. Since polarization charges on the skin cannot have an effect in this case, any modulation occurring must be due to the polarization currents. The origin of the currents does not matter, so that they may as well be introduced by contact electrodes, since this arrangement affords easier control of the current magnitude for research purposes. An experiment was done in which currents in the tissue were produced by contact electrodes (3M red dot$^{tm}$, 22×22 mm) placed on the skin at the back of the right knee, with a center-to-center separation of 45 mm, such as to expose the underlying sciatic nerve to longitudinal currents. For a sinusoidal current with a peak density amplitude of 3.4 nA/cm$^2$ at a frequency of 2.410 Hz, the 100–60 counts were 33 s at t=0, 54 s at t=20 minutes, and 67 s at t=40 minutes, showing excitation of the 2.4 Hz resonance. The current density of 3.4 nA/cm$^2$ is much too small for causing classical nerve stimulation. No excitation was found for a similar current injection transverse to the nerve. The experiments show that indeed, afferent fibers in a nerve can be modulated by electric currents without undergoing classical nerve stimulation. The current densities at which modulation occurred were a factor 10 larger than in the previously discussed experiment with the dorsum of the foot, wherein the 2.4 Hz resonance was not excited. The finding that transverse currents do not excite the resonance shows that the modulation is really done on the afferent fibers, and not on receptors.

Similar results were found for sinusoidal current applications to the skin over the right vagus nerve in the neck. Exposure to longitudinal currents in the range from 200 pA/cm$^2$ to 60 nA/cm$^2$ caused excitation of the 2.4 Hz resonance, but transverse currents showed no effect. The fact that the current density of 200 pA/cm$^2$ caused excitation of the resonance while 321 pA/cm$^2$ applied to the dorsum of the foot was ineffective is understandable as due to the bulk effect discussed above; the afferents are much more numerous in the vagus nerve than in the affected region in the foot experiment. To get further data on this issue, we measured the effective intensity window for excitation of the 2.4 Hz resonance through vagal modulation with longitudinal currents applied by contact electrodes attached to the overlying skin. The contact electrodes used were again a pair of 3M red dot™ electrodes with centers 45 mm apart. To provide longitudinal currents, the electrodes were placed on the skin of the neck over the right vagus nerve, one above the other along the direction of the underlying nerve. The results are shown in FIG. 14, where the time needed for the silent count from 100 to 70 is plotted versus the amplitude of the total current passed through the subject by the contact electrodes placed on the neck. The current was sinusoidal with frequency of 2.466 Hz. For a fixed current amplitude, the 100–70 counting time was measured at the beginning, t=0, of the current application, at t=20 minutes into the experiment run, and at t=40 minutes at the end of the run. In FIG. 14 the measured counting times are shown as graph 73 for t=0, graph 74 for t=20 minutes, and graph 75 for t=40 minutes. The effective intensity window is clearly seen to extend from about 100 pA to about 200 nA. The apparant anomaly near point 74 is attributed to chemical detuning. Dividing by the electrode area of 484 mm$^2$, the window for the peak current density in the subject is found to range from 21 pA/cm$^2$ to 41 nA/cm$^2$. These current densities are much too small to cause classical nerve stimulation. The previously discussed modulation mechanism involving the Debye layer in the epidermis does not apply in this case since the modulation does not involve receptors, but rather afferent fibers in a nerve that runs in the tissue underlying the skin region of the current injection. It must be that longitudinal electric currents in the tissue surrounding the vagus nerve can affect the propagation velocity of action potentials in the afferents; fluctuating applied currents would then result in frequency modulation of the spike trains received by the brain. Since the propagation velocity of action potentials along an axon is influenced by the membrane conductance, and the latter is a sensitive function of the membrane potential [38], the propagation speed can indeed be modulated by perturbations of the membrane potential brought about by longitudinal currents superimposed on the currents that accompany the action potential propagation, considering the nonuniformities of conductivity in the current path distribution. The modulations of propagation speed brought on by the currents are very small, but they can produce a fm of signals received by the brain that suffices for the excitation of a sensory resonance, if the frequency of the current is chosen properly. The influencing of the action potential propagation speed along an axon by an external electric field is of great importance to neural science and needs to be investigated further.

Further experimentation has shown that sensory resonances can be excited by external fluctuating electric fields with amplitudes on the skin much lower than 1 V/m. This was already known from experiments with the ½ Hz resonance which shows ptosis of the eyelids occurring at field amplitudes of 20 mV/m on the skin, using a doublet placed some distance from the subject, such as to expose a large area of skin to the weak field. The discovery of the 2.4 Hz resonance with the more sensitive and quantitative detector in the form of the silent count made measurements at even lower field strengths possible. In these experiments a doublet with rectangular field electrodes of 59×44 cm was used, oriented as in FIG. 12. The doublet was driven by a sine wave with amplitude of 1.25 V, at a frequency near 2.4 Hz.

The doublet was placed at various distances from the subject, about at hip height. The distances were large enough to expose a large skin area to the field. The maximum field induced on the subject's skin was estimated with Eq. (25), using a 24 cm radius sphere to model the subject. The results for the silent 100–40 count are shown in FIG. 15, where the counting time at the beginning, t=0, of the run, at t=20 minutes, and t=40 minutes is shown respectively by graphs 76, 77, and 78. The crossover of graphs 77 and 78 is attributed to chemical detuning. A pronounced slowing of the counting is seen to occur already at a peak field external field amplitude of 10 mV/m. FIG. 15 shows an effective intensity window that extends from about 8 to 190 mV/m field amplitude. With Eqs. (26)–(28), using the values for s/α for the experiments together with FIG. 12, the effective intensity window can be expressed in terms of the polarization current in the subject's body; the window is found to extend from 0.25 to 5.9 pA.

Since in the experiments the distance s of FIG. 12, measured from the center of the doublet to the subject's body, varied from 64.5 cm to 208 cm, there was considerable variation of the skin area $A_s$ of predominant field application, which in first approximation is proportional to $s_2$. Therefore it is of interest to consider the bulk effect discussed above. Using Eqs. (15) and (16), ignoring the effect of the surface density ρ of cutaneous nerves, and taking $\sqrt{A_s}$ as the distance s of FIG. 12, the graphs of FIG. 15 may be replotted in terms of the quantity $E_{max}s$. The result is shown in FIG. 16, where the graphs for t=0, 20, and 40 minutes are shown respectively as 79, 80, and 81. The effective intensity window is seen to extend from about 17 to 123 mV, in terms of $E_{max}s$. That the voltages are comparable to membrane potentials is deemed fortuitous.

In the above experiment, different field strengths were obtained by putting the doublet at different distances s from the subject. This resulted of course in different areas $A_s$ of predominant field application. As a check on the validity of Eq. (15), an experiment was performed in which $A_s$ is fixed, and the field strength is varied by changing the voltage applied to the field electrodes. The latter were a shielded pair as in FIG. 10, with field electrodes of 223×230 mm applied to the thighs of the subject at a distance of 5 mm from the skin. A sinusoidal generator voltage was used with frequency of 2.408 Hz and an amplitude of 1.25 V. Before application to the electrodes, the generator output voltage was reduced by an adjustable voltage divider. Silent counts from 100 to 60 were done at times t=0, 20, and 40 minutes into the experiment run. The resulting counting times are plotted as function of $E\sqrt{A_s}$, where $A_s$ is the skin area of predominant field application, which here is equal to the electrode area of 513 cm$^2$. E is the electric field on the skin apposing the field electrode; E is uniform and equal to $E_{max}$ introduced above. The resulting plots are shown in FIG. 17, where 82, 83, and 84 are respectively the counting time plots for t=0, 20, and 40 minutes. The anomaly at the data points with $E\sqrt{A_s}$=79.5 may perhaps be attributed to chemical detuning that depresses the counting times, but the matter needs further investigation. The data reveal an effective intensity window that extends from 18.2 to 158 mV in terms of $E\sqrt{A_s}$. Comparison with FIG. 16 shows that the windows for the two experiments are in rather good agreement, considering the crudeness of the model illustrated in FIG. 12, and the neglect of differences in surface density ρ of cutaneous nerves in the skin areas involved; see Eqs. (15) and (16).

In order to see the effect of surface density ρ of cutaneous receptors, another experiment was done in which a shielded pair of small field electrodes was applied to the tip of the index and middle fingers of the left hand. Since the receptor density ρ is larger on the finger tips than on the thighs, the values for $E_{max}\sqrt{A_s}$ in the window are expected to be less than for the thighs experiment. The field electrode area was 15×20 mm, and both field electrodes were applied at an average distance d=0.5 mm from the skin, accounting for the distance variation due to the ridges on the fingerprint skin. The voltage applied to the field electrodes (2 and 2' of FIG. 10) was sinusoidal with an amplitude of 1.15 V, reduced by a resistive divider, so that different field electrode voltages can be applied from run to run. Counting times from 100 to 60 are plotted in FIG. 18 versus $E_{max}\sqrt{A_s}$. The graphs 85, 86, and 87 show respectively the counting times at t=0, 20, and 40 minutes into the run. The data reveal an effective intensity window that extends from 6.6 to 54 mV, in terms of $E_{max}\sqrt{A_s}$. The bimodality of graphs 86 and 87 does not appear to be due to chemical detuning, and needs to be investigated further. Comparison with FIG. 17, where the window extends from 18.2 to 158 mV, and use of Eqs. (15) and (16), gives for the surface densities the ratio $$\rho_f/\rho_t=2.9, \tag{30}$$

where $\rho_f$ and $\rho_t$ are respectively the receptor densities of the affected cutaneous nerves on the finger tips and on the thighs. The upper window limits have been used in calculating the ratio (30).

The small ratio (30) is surprising, and it may help in identifying which type afferents are modulated. There are four different kinds of nerve endings in fingerprint skin: bare intraepidermal terminals, intrapapillary coils, Merkel cells, and Meissner corpuscules [34]. The latter have poor low frequency response. The Merkel cells are mechanoreceptors that are innervated by slow-adapting (SA) afferents with good low frequency response, which makes them candidates for electric field modulation with the frequencies used. The cells sometimes are found to be most profuse near the entry of sweat ducts into the underside of the epidermis [34]. Nearby Merkel cells are thus subjected to a field that is concentrated by the conductive sweat ducts, so that they may get modulated. The matter needs further investigation.

It is of interest to compare the ratio of upper to lower limit of the windows, as it is independent of the receptor density ρ; this ratio is here called the span of the window. For FIGS. 16, 17, and 18, the span is found to be respectively 7.2, 8.7, and 8.2. The good agreement of the spans of the effective intensity windows for the three experiments with different skin areas of predominant field application supports the notion that the nuisance-guarding circuitry is the same in all three cases. In contrast, the window span is about 2000 in FIG. 14 which pertains to excitation not by external electric fields, but by longitudinal currents applied with contact electrodes to the skin overlying the vagus nerve in the neck. Our comments on this large span of 2000 are as follows. First, the afferents in the vagus nerve report visceral information, whereas the cutaneous nerve signals are somatosensory. Since the latter are much more prone to nuisance signals coming from the environment, the nuisance-guarding circuitry involved is expected to be more sensitive. It is even somewhat surprising that such activity is indicated at all for visceral information. Second, our modulation of the vagus nerve and cutaneous nerves are of different nature, as evidenced by the large current densities needed in the former case. Perhaps the modulation of the propagation speed along the afferents involved is a strongly nonlinear function of the applied longitudinal current density.

Although an effective intensity window has been noticed in the ½ Hz experiments, the window has not been measured, mainly because we lacked a sensitive quantitative indicator. Ptosis of the eyelids, the leading indicator for the ½ Hz resonance, is not nearly as suitable a detector as the 100–60 counting time for the 2.4 Hz resonance. In the absence of the full window information, one can still see whether effective intensities for the ½ Hz resonance fit the 2.4 Hz windows, in terms of $E_{max}\sqrt{A_s}$. For the ½ Hz cases we take two experiments with setups that have given satisfactory results as sleeping aids. The first of these is illustrated by FIG. 1, with the peak external electric field amplitude on the skin estimated as 1 V/m. With the area $A_s$ of predominant field application estimated as 400 cm², the product $E_{max}\sqrt{A_s}$ comes to 200 mV. The second experiment involves a doublet of 16 cm² area driven by 3 V peak to peak, and placed at a distance s=30 cm from the subject's thighs. Use of Eqs. (25) and FIG. 12 gives for the maximum electric field on the skin $E_{max}$=12 mV/m, so that one has $E_{max}\sqrt{A_s}$=4 mV, using $\sqrt{A_s}$=s. The $E_{max}\sqrt{A_s}$ values of 200 mV and 4 mV for these ½ Hz resonance cases can perhaps be reconciled with the 2.4 Hz resonance window of FIG. 16, considering differences in the density ρ of affected cutaneous receptors in the skin areas of predominant field application involved. This result supports the notion that the nuisance-guarding circuitry is the same for the ½ Hz and 2.4 Hz resonances. Further experiments are needed to settle the question.

For a sinusoidal external field the polarization current density in the skin has approximately the amplitude $$j=2\pi f \epsilon_o E_o, \tag{31}$$

where $E_O$ is the external field on the skin, $f$ the field frequency, and $\epsilon_o$ the permittivity of free space. For the ½ Hz experiment discussed in regard to Eqs. (4)–(9), the current density amplitude (31) comes to 2.8 fA/cm². This value is of course very much smaller than the peak current density of 17 pA/cm² given by (9) for the rounded square wave. It has been observed that, in weak field experiments with cutaneous nerves, sine waves excite the resonance just as well as square waves of the same amplitude, rounded or not. This is consistent with our conclusion that it are the polarization charges that cause the modulation of the cutaneous nerves, not the polarization currents. Since the polarization currents constitute a foreign intrusion, sine waves, with their mimimum polarization currents, are to be preferred from a neurological point of view.

Excitation of the ½ Hz resonance is possible with large external electric fields, up to 10 KV/m, produced by placing insulated field electrodes directly on the skin of the thighs. In this arrangement, a sweat layer quickly develops between the skin and the field electrode insulation. This highly conductive layer removes the polarization charges from the skin so that the mechanism that relies on the Debye smearing of the polarization charges in the epidermis cannot operate. Therefore, the modulation of cutaneous nerves in this case must be due to polarization currents. For the rounded square wave used, the peak polarization current density in the skin apposing the field electrodes is found to have an amplitude of about 100 nA/cm². This current density lies somewhat outside the window of FIG. 14, which ranges from 21 pA/cm² to 41 nA/cm², in terms of the current density. The discrepancy is believed to be due to the difference in the density of afferents for the two cases. Since the afferents of the cutaneous nerves in the dermis are oriented roughly perpendicular to the skin surface, the local polarization current is longitudinal with respect to the afferent fibers, so that one expects the afferents to be subject to modulation by the currents, at least by virtue of the action potential propagation speed effect discussed. In addition, the cutaneous receptors may also respond to the large polarization currents. The modulation of cutaneous nerves by the large external field of 10 KV/m in the presence of a sweat layer between skin and field electrode insulation is thereby understood to about the same extent as the other modulation situations. It is emphasised that the polarization current density of 100 nA/cm$^2$ is still much too small to cause classical nerve stimulation.

Dominant frequencies appropriate for the excitation of sensory resonances discussed lie near ½ Hz and 2.4 Hz. Additional sensory resonances may be found, with frequencies up to perhaps 45 Hz.

Strong fields applied to areas of skin overlying nerves may be used for modulating afferent fibers in these nerves, thereby providing a method for manipulation of the nervous system via visceral afferents, as in the vagus nerve. The method differs from that of Wernicke et al. [36] and from that of Terry et al. [37], in that it employs field electrodes rather than contact electrodes, so that it is noninvasive, and there is no reliance on classical nerve stimulation, so that current densitites smaller by a factor 50000 suffice. Furthermore, the present invention uses excitation of sensory resonance. In our experiments, a shielded pair of insulated field electrodes is placed on or adjacent to the skin such that the line connecting their centers is roughly parallel to the underlying nerve, afferents of which are to be modulated. The field strength needed for the excitation of sensory resonances can be calculated from (31) if the necessary current densities are known. For the excitation of the 2.4 Hz resonance through the vagus nerve, these current densities can be determined from FIG. 14; accounting for the electrode area of 484 mm$^2$, the window extends from 21 pA/cm$^2$ to 41 nA/cm$^2$. Using (31), the corresponding field strengths for a sine wave are found to range from 3.8 KV/m to 7.6 MV/m. A low-voltage sine wave generator suffices for the production of fields in a low part of this range, if the insulated field electrodes are placed directly on the skin. For instance, with insulating tape 0.076 mm thick (3M Scotch™ Mailing Tape), a voltage amplitude of 1 V gives a field of 13.2 KV/m.

Strong-field experiments have been conducted on the sciatic nerve underlying the skin on the back of the knee, using an insulated doublet of 60×42 mm area. With the doublet positioned in the skin fold of the bent knee, and an 162×135 mm insulation sheet provided such that the polarization currents cannot be shortened by apposing skin of calf and thigh, the sciatic nerve was exposed to longitudinal polarization currents of the order of 50 pA/cm$^2$, caused by fields of about 3.7 KV/m set up by a sine wave voltage of 1.13 V amplitude at a frequency of 2.414 Hz. The 100 to 60 counting times were 34 s at t=0, 54 s at t=20 minutes, and 59 s at T=40 minutes, showing that the 2.4 Hz resonance was excited.

A similar experiment was done in the right armpit, exposing the ulnar nerve to longitudinal polarization currents that were caused by the 60×42 mm doublet inbedded in the 162×135 mm insulation sheet discussed above, using the same voltage amplitude and frequency as before. The 100–60 counting times were 33 s at t=0, 57 s at t=20 minutes, and 57 s at t=40 minutes, showing excitation of the 2.4 Hz resonance.

Finally, a strong-field experiment was done on the right vagus nerve in the neck, using a shielded pair of field electrodes of 22×22 mm area, at a center-to-center distance of 45 mm, oriented such as to expose the nerve to longitudinal polarization currents. The field electrodes were driven by a sinusoidal voltage with an amplitude of 1.13 V and a frequency of 2.414 Hz. The 100–60 counting times were 34 s at t=0, 68 s at t=20 minutes, and 74 s at t=40 minutes, showing excitation of the 2.4 Hz resonance. In spite of the rather close proximity of the skin area of predominant field application, the brain was not subjected to substantial polarization current densities, by virtue of the strict field localization by the shielded field electrode pair.

The experiments discussed show that there are two regimes of afferents modulation by an electric field applied to a selected skin area. The first regime involves modulation of cutaneous sensory receptors by polarization charges in the skin, and is therefore called charge modulation. In the second regime the polarization currents are strong enough to cause modulation of the propagation speed of action potentials along axons exposed to the currents, so that the regime is called current modulation. In both regimes, the polarization currents are much too weak to cause classical nerve stimulation. Sensory resonances can be excited in both regimes, but the effective intensity windows have different spans. In the charge modulation regime, the window extends roughly from 20 mV to 140 mV in the parameter $E_{max}\sqrt{A_s}$, to be adjusted for different densities of the affected cutaneous receptors. In the current modulation regime, the effective intensity window extends roughly from 21 pA/cm$^2$ to 41 nA/cm$^2$, to be adjusted for the number of affected afferents in the nerve exposed to the polarization currents. The span of about 2000 for this window compared to about 8 for the charge modulation regime shows that different mechanisms operate in the two regimes. Current modulation is suitable for manipulation of the nervous system through visceral or somatosensory afferents in large nerves that are, at places, capacitively accessible through the skin, such as vagus and sciatic nerves. In these cases, the application of external fields can be done with a shielded pair of field electrodes, placed on the overlying skin in the direction of the nerve. When used properly, the shielded electrode pair assures that the field is applied strictly to the underlying skin, without exposing more distant regions of the body, such as the brain, to substantial polarization currents. The field strengths appropriate for exitation of sensory resonances in the two regimes differ by a large factor; for charge modulation, typical fields on large skin areas range from 10 to 200 mV/m, whereas for the current modulation the fields, naturally for localized small skin area exposure, are of the order of kilovolts per meter. For both regimes, the proper fields can be produced by the same low-voltage generator, simply by using different field electrodes and deployment. The doublet placed some distance from the subject is particularly suitable for charge modulation of cutaneous receptors over large skin areas, whereas the shielded pair is the field electrode configuration of choice in the current modulation regime, although a single doublet may be used for the special case where it can be completely surrounded by the subject's skin.

The method is expected to be effective also on certain animals, and applications to animal control are therefore envisioned. The nervous system of mammals is similar to that of humans, so that sensory resonances are expected to exist, albeit with somewhat different frequencies. The disposition toward the ½ Hz resonance is thought to have its origin in the fetal state, developed by the rythmical sensations caused by the mother's walk, associatively coupled with hormone concentrations. For mammals, one expects a resonance of this type at about the frequency of the mother's relaxed walk. Accordingly, in the present invention, the subjects are mammals.

The invention is not limited by the embodiments shown in the drawings and described in the specification, which are given by way of example and not of limitation, but only in accordance with the scope of the appended claims.

REFERENCES

[1] ELECTRICAL STIMULATION RESEARCH TECHNIQUES, Ed. M. M. Patterson and R. P. Kesner, Academic Press, New York, 1981

[2] NEUROSTIMULATION AN OVERVIEW Ed. Y. Lazorthes and A. R. M. Upton, Futura Publ. Co., Mt. Kisco, N.Y., 1985

[3] A. Sances, Jr. and S. J. Larson, ELECTROANESTHESIA, Academic Press, New York, 1975

[4] D. L. Guyton and F. T. Hambrecht, "Capacitor Electrode Stimulates Nerve or Muscle without Oxidation-Reduction Reactions", Science 181, 74 (1973)

[5] A. Mauro, "Capacity Electrode for Chronic Stimulation", Science 132, 356 (1960)

[6] J. B. Ranck, Jr. "Extracellular Stimulation" in [1]

[7] J. E. Swett and C. M. Bourassa, "Electrical Stimulation of Peripheral Nerve" in [1]

[8] Y. Morita, H. Seno, K. Nagata, N. Ishikawa, J. Matsumoto, and K. Mori, "Assessment of Efficacy of Electrosleep in Clinical Application", in ELECTROSTIMULATION, Proceedings of the Sixth International Symposium on Electrostimulation, Albena, Bulgaria. Ed. V. Ivanov, MA-Center, Sofiya, 1981

[9] M. Hutchison, MEGABRAIN, Ballantine Books, New York, 1991

[10] Norbert Wiener, NONLINEAR PROBLEMS IN RANDOM THEORY, p. 71–72, John Wiley & Sons, New York, 1958

[11] M. J. W. Brennan, U.S. Pat. No. 5,169,380 (1992)

[12] R. Stone, "Polarized Debate: EMFs and Cancer", Science 258, 1724 (1992)

[13] E. R. Kandel, J. H. Schwartz, and T. M. Jessell, PRINCIPLES OF NEURAL SCIENCE, 3d Edition, Elsevier, New York, 1991

[14] Scientific American, October 1992, p. 14

[15] R. O. Becker and A. A. Marino, ELECTROMAGNETISM AND LIFE, State University of New York Press, Albany, 1982

[16] P. L. Nunez, ELECTRIC FIELDS OF THE BRAIN, Oxford University Press, 1981

[17] B. Katz, NERVE, MUSCLE, AND SYNAPSE, p. 46–47, McGraw-Hill, New York, 1966

[18] H. F. Bradford, CHEMICAL NEUROBIOLOGY, W. H. Freeman and Co., New York, 1986

[19] AMERICAN INSTITUTE OF PHYSICS HANDBOOK, McGraw-Hill, New York, 1957

[20] S. Ohki and H. Oshima, "Donnan Potential and Surface Potential of a Charged Membrane and Effect of Ion Binding on the Potential Profile" in ELECTRICAL DOUBLE LAYERS IN BIOLOGY, Ed. M. Blank, Plenum Press, New York, 1986

[21] HANDBOOK OF SENSORY PHYSIOLOGY, VOL II, Somatosensory System, Ed. A. Iggo, Chapter I, Springer, New York, 1973

[22] H. Hensel, THERMAL SENSATIONS AND THERMORECEPTORS IN MAN, Charles C. Thomas, Springfield, Ill. 1982

[23] A. Iggo, "Sensory Receptors, Cutaneous", in SENSORY SYSTEMS II SENSES OTHER THAN VISION, Ed. J. M. Wolfe, Birkhauser, Boston, 1988

[24] M. S. Laverack and D. J. Cosens, SENSE ORGANS, Chapter 17, Blackie, London, 1984

[25] C. A. Terzuolo and T. H. Bullock, "Measurement of Imposed Voltage Gradient Adequate to Modulate Neuronal Firing", Proceedings of the National Academy of Sciences U.S.A., Physiology, 42, 687 (1956)

[26] A. Longtin and K. Hinzer, "Encoding with Bursting, Subthreshold Oscillations, and Noise in Mammalian Cold Receptors", Neural Computation 8, 215 (1996)

[27] A. Sommerfeld, ELECTRODYNAMICS, Academic Press, New York, 1952

[28] P. M. Morse and H. Feshbach, METHODS OF THEORETICAL PHYSICS, McGraw-hill, New York, 1953

[29] G. H. Golub and C. F. Van Loan, MATRIX CALCULATIONS, 2nd Ed., John Hopkins University Press, Baltimore, 1991

[30] Basic Stamp, PARALAX, INC. Rocklin, Calif. 95765

[31] Don Lancaster, CMOS COOKBOOK, 1st Ed., p. 327, Howard W. Sams & Co., Indianapolis, 1977

[32] J. G. Graeme, APPLICATIONS OF OPERATIONAL AMPLIFIERS, FIG. 5.4, p. 149, McGraw-Hill, New York, 1973

[33] A. R. Bulsara and L. Gammaitoni, "Tuning in to Noise", Physics Today, 49, No. 3, p. 39 (1996)

[34] T. A. Quilliam, "Neuro-Cutaneous Relationships in Fingerprint Skin", THE SOMATOSENSORY SYSTEM, Ed. H. H. Kornhuber, p. 193, George Thiemer Verlag, Stuttgart, 1975

[35] C. van Vreeswijk and H. Sompolinsky, "Chaos in Neural Networks with Balanced Excitatory and Inhibitory Activity", Science 274, 1724 (1996)

[36] J. F. Wernicke et al., U.S. Pat. No. 5,269,303 (1993)

[37] R. S. Terry, Jr. et al., U.S. Pat. No. 5,335,657 (1994)

[38] A. L. Hodgkin and A. F. Huxley, "Current carried by sodium and potassium ions through the membrane of the giant axon of Logio", Journal of Physiology 116, 449 (1952)

I claim:

1. Electric field generator for manipulating the nervous system of a subject, which comprises:

generator means for generating a fluctuating voltage;

at least one doublet having two field electrodes such as to form a parallel-plate condensor;

distributor means, responsive to the fluctuating voltage, for charging said at least one doublet;

said at least one doublet to be positioned and oriented such as to render the subject entirely outside the parallel-plate condensor.

2. The electric field generator of claim 1, further including:

passive doublet having two field electrodes such as to form a parallel-plate condensor;

a conductor connecting last said two field electrodes;

the passive doublet being positioned outside first said parallel-plate condenser, such that one of last said two field electrodes is apposed to one of first said two field electrodes.

3. The electric field generator of claim 1, further including a dielectric placed between the two field electrodes.

4. The electric field generator of claim 1, further including casing means for containing the generator means, the distributor means, and said at least one doublet.

5. A method for manipulating the nervous system of a subject, comprising the steps of:

generating a fluctuating voltage;

constructing a doublet having two field electrodes such as to form a parallel-plate condensor;

applying the fluctuating voltage between said two field electrodes to induce an electric field; and placing the doublet such as to expose the subject solely to the electric field outside the parallel-plate condenser.

6. The method of claim 5, further including the steps of:

constructing another doublet having two field electrodes such as to form a parallel-plate condenser;

connecting last said two field electrodes to each other;

placing said another doublet outside first said parallel-plate condensor, such that one of last said two field electrodes is apposed to one of first said two field electrodes;

whereby the electric field polarizes said another doublet; and whereby said another doublet induces an electric field which boosts first said electric field at large distances.

7. The method of claim 5, for exciting in the subject a sensory resonance, the sensory resonance having a resonance frequency, and wherein the fluctuating voltage has a frequency, the method further including the step of setting the voltage frequency to the resonance frequency.

8. Electrode for use in an electric field generator for manipulating the nervous system of a subject, comprising:

an input port;

at least one doublet having two field electrodes such as to form a parallel-plate condenser;

distributor means, connected to the input port, for charging said at least one doublet when the input port is energized;

said at least one doublet to be positioned and oriented such as to render the subject entirely outside the parallel-plate condensor.

9. The electrode of claim 8, further including a dielectric placed between the two field electrodes.

* * * * *